US007951926B2

(12) United States Patent
Morvan et al.

(10) Patent No.: US 7,951,926 B2
(45) Date of Patent: May 31, 2011

(54) METHOD FOR THE SYNTHESIS OF OLIGONUCLEOTIDE DERIVATIVES

(75) Inventors: François Morvan, Castelnau le Lez (FR); Albert Meyer, Perols (FR); Jean-Jacques Vasseur, Combaillaux (FR); Sébastien Vidal, Villeurbanne (FR); Jean-Pierre Cloarec, Lyons (FR); Yann Chevolot, Fleurieux sur l'Arbresle (FR); Eliane Souteyrand, Chambon sur Cisse (FR)

(73) Assignee: Centre National de la Recherche Scientifique (CNRS) (FR)

( * ) Notice: Subject to any disclaimer, the term of this patent is extended or adjusted under 35 U.S.C. 154(b) by 159 days.

(21) Appl. No.: 12/298,824

(22) PCT Filed: Apr. 26, 2007

(86) PCT No.: PCT/IB2007/002486
§ 371 (c)(1),
(2), (4) Date: Dec. 18, 2008

(87) PCT Pub. No.: WO2007/125429
PCT Pub. Date: Nov. 8, 2007

(65) Prior Publication Data
US 2009/0124571 A1 May 14, 2009

Related U.S. Application Data

(60) Provisional application No. 60/745,905, filed on Apr. 28, 2006.

(51) Int. Cl.
C07H 21/00 (2006.01)
C07H 21/02 (2006.01)
C12Q 1/68 (2006.01)
(52) U.S. Cl. .................. 536/23.1; 536/24.3; 536/25.3; 536/26.6; 435/6

(58) Field of Classification Search ............ 536/23.1, 536/24.3, 25.3, 26.6; 435/6
See application file for complete search history.

(56) References Cited

OTHER PUBLICATIONS

International Search Report and Written Opinion for PCT/IB2007/002486 filed Apr. 26, 2007.
Kolb H C et al: "The growing impact of click chemistry on drug discovery"; Drug Discovery Today, Elsevier, Rahway, NJ, US; vol. 8, No. 24; Dec. 15, 2003; pp. 1128-1137; XP002377521.
Seo T S et al: "Click chemistry to construct fluorescent oligonucleotides for DNA sequencing"; Journal of Organic Chmeistry; American Chemical Society; Easton; vol. 68; Jan. 1, 2003; pp. 609-612; XP002977877.
Singh Yashveer et al: "Preparation of a multitopic glycopeptides-oligonucleotide conjugate"; Organic Letters; vol. 7, No. 7; Mar. 2005; pp. 1359-1362; XP002491161.
Devaraj N K et al: "Chemoselective covalent coupling of oligonucleotide probes to self-assembled monolayers"; Journal of the American Chemical Society 200050622 US; vol. 127, No. 24; Jun. 22, 2005; pp. 8600-8601; XP002491162.

(Continued)

*Primary Examiner* — Jezia Riley
(74) *Attorney, Agent, or Firm* — Alston & Bird LLP

(57) ABSTRACT

Method for the synthesis of nucleotide derivatives wherein molecules of interest are grafted on the oligonucleotide with the help of a "click chemistry" reaction between an azide function on the molecule of interest and an alkyne function on the oligonucleotide, or between an alkyne function on the molecule of interest and an azide function on the oligonucleotide.
Intermediate molecules, notably alkyne functionalized oligonucleotides, grafted oligonucleotides, azide functionalized oligonucleotides, oligonucleotide micro arrays containing them and the use of those grafted oligonucleotides for biological investigation and for cell targeting.

17 Claims, 24 Drawing Sheets

OTHER PUBLICATIONS

Burley Glenn A et al: "Directed DNA metallization"; Journal of the American Chemical Society, Washington, DC; vol. 128, No. 5; Jan. 12, 2006; pp. 1398-1399; XP002397907.

Wang Qian et al: "Bioconjugation by copper (I)-catalyzed azide-alkyne [3+2] cycloaddition"; Journal of the American Chemical Society, American Chemical Society, Washington, DC, US; vol. 125, No. 11; Feb. 22, 2003; pp. 3192-3193; XP002377520.

Wu P et al: "Efficiency and Fidelity in a Click-Chemistry Route to Triazole Dendrimers by the Copper (I)-Catalyzed Ligation of Azides and Alkynes"; Angewandte Chemie. International Edition, Wiley VCH Verlage, Weinheim; vol. 43; Jan. 1, 2004; pp. 3928-3932; XP002351095.

Appukkuttan Prasad et al: "A microwave-assisted click chemistry synthesis of 1,4-disubstituted 1,2,3-trizaoles via a copper (I)-catalyzed three-component reaction"; Organic Letters, ACS, Washington, DC; vol. 6, No. 23; Nov. 11, 2004; pp. 4223-4225; XP002472070.

Bouillon C et al: "Microwave assisted "click" chemistry for the synthesis of multiple labeled-carbohydrate oligonucleotides on solid support"; Journal of Organic Chemistry 20060609 US; vol. 71, No. 12, Jun. 9, 2006; pp. 4700-4702; XP002491163.

Chevolot Yann et al: "DNA-based carbohydrate biochips: a platform for surface glycol-engineering."; Angewandte Chemie (International Ed. in English) 2007; vol. 46, No. 14, 2007; pp. 2398-2402; XP002491164.

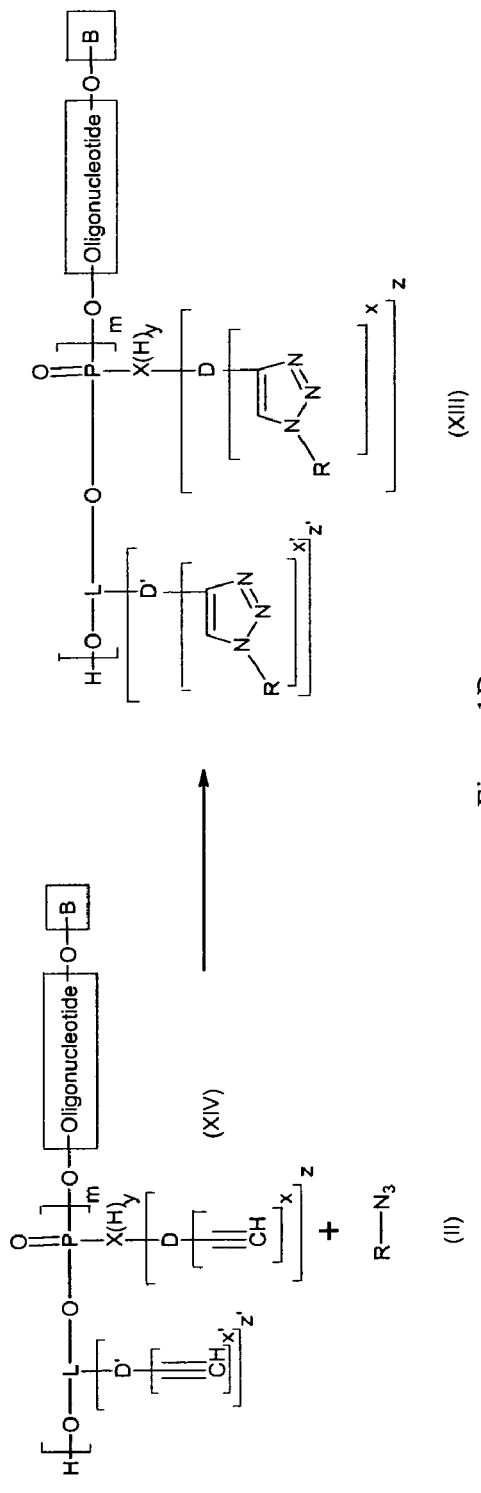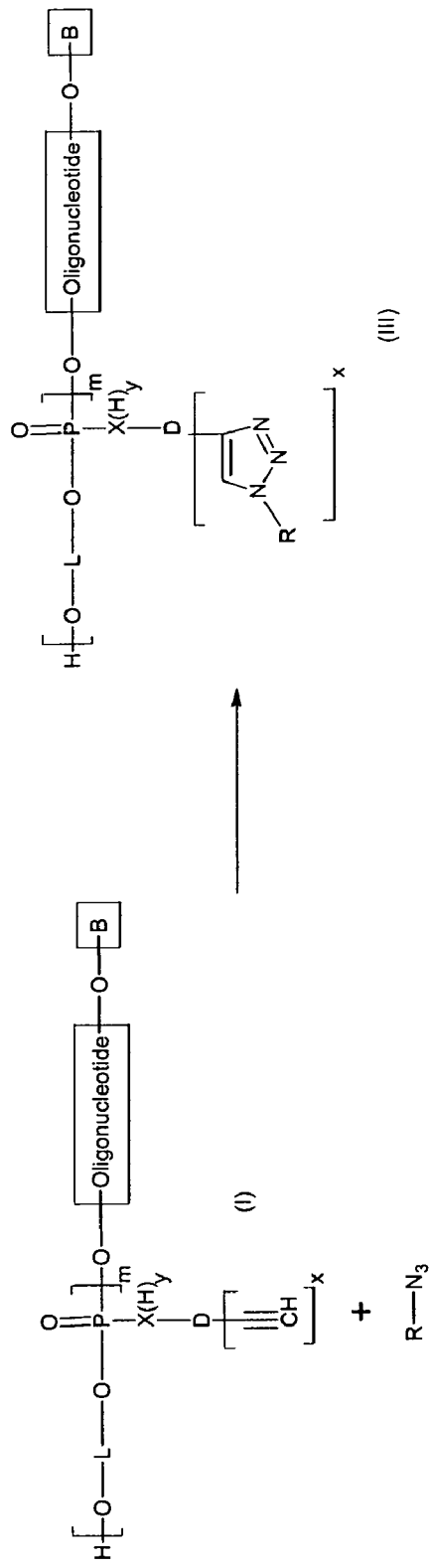
Figure 1B
Figure 1A

Cne: cyanoethyl
DMTr: 4, 4'-dimethoxytrityl
iPr: isopropyl

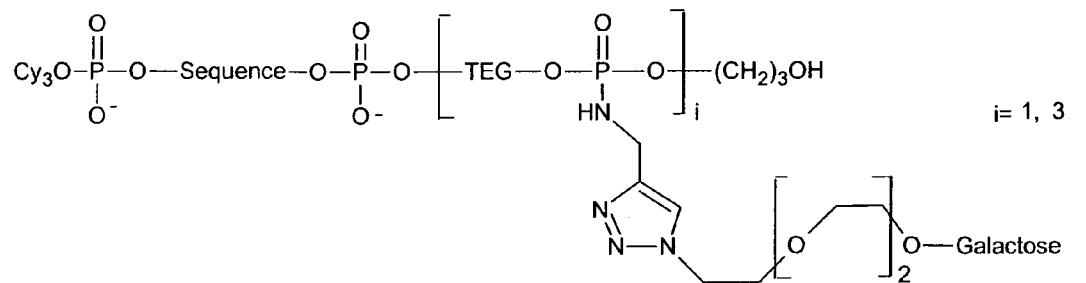
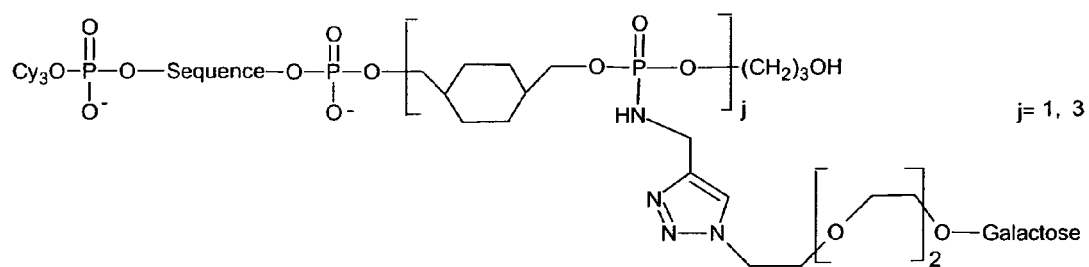
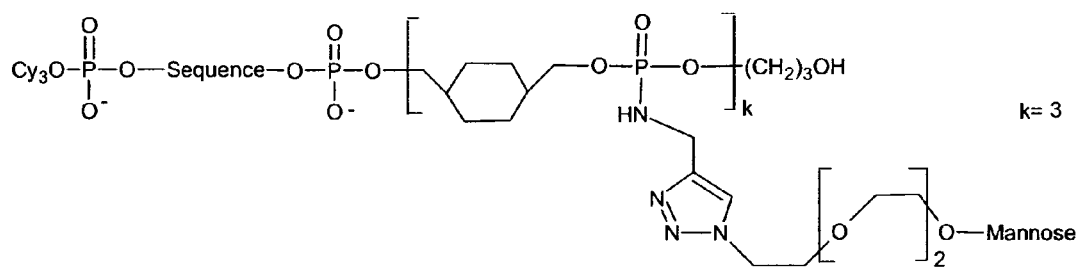
Sequence = 5'-CTG CCT CTG GGC TCA-3'
Figure 7

Figure 8:
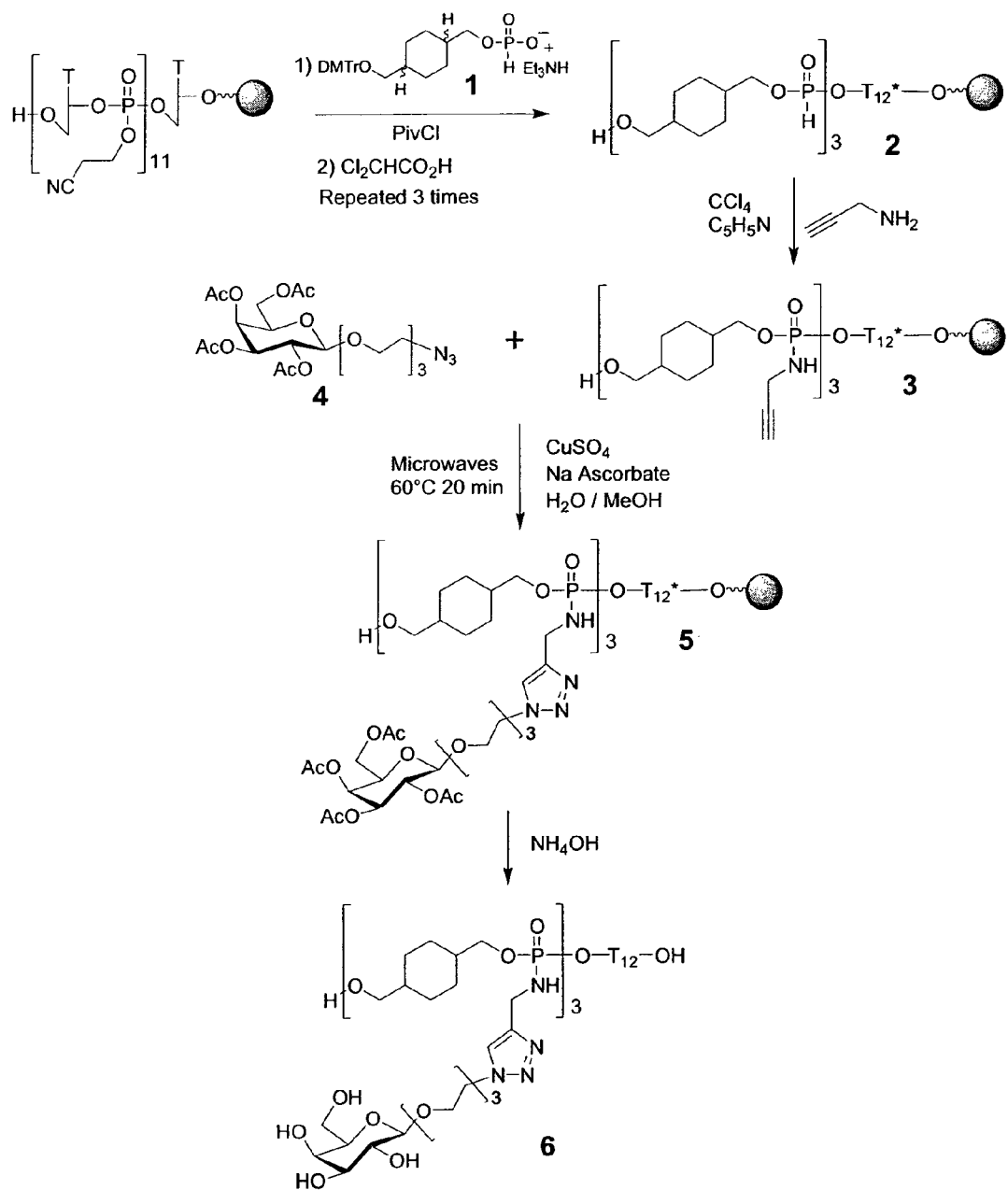

Figure 8 : Solid-supported synthesis of a $T_{12}$ *tris*-propargyl-phosphoramidate oligonucleotide 3 and its conjugation to galactosyl azide 4 by microwave assisted click chemistry.

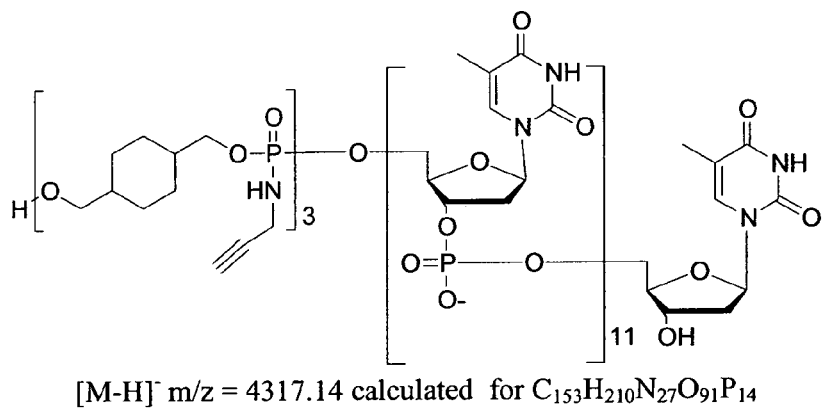
[M-H]⁻ m/z = 4317.14 calculated for $C_{153}H_{210}N_{27}O_{91}P_{14}$
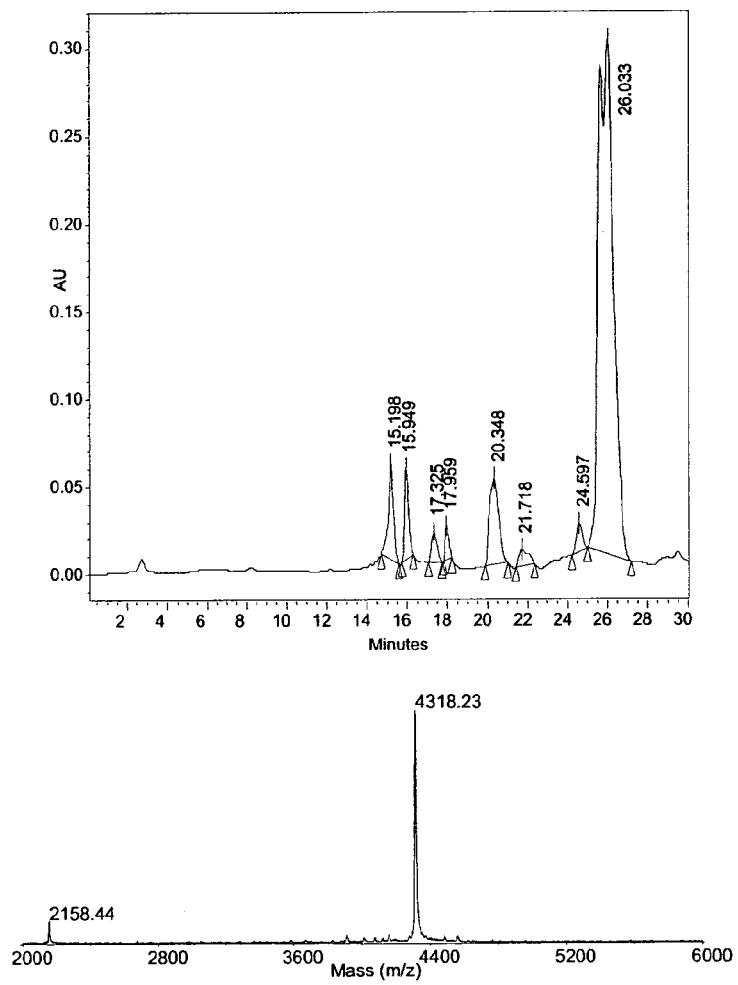
Figure 10
HPLC and MALDI-TOF MS (THAP as matrix) of crude 3 after aqueous ammonia treatment DMTr = 4,4'-dimethoxytrityl, Cne = cyanoethyl n=1,2

Figure 13:
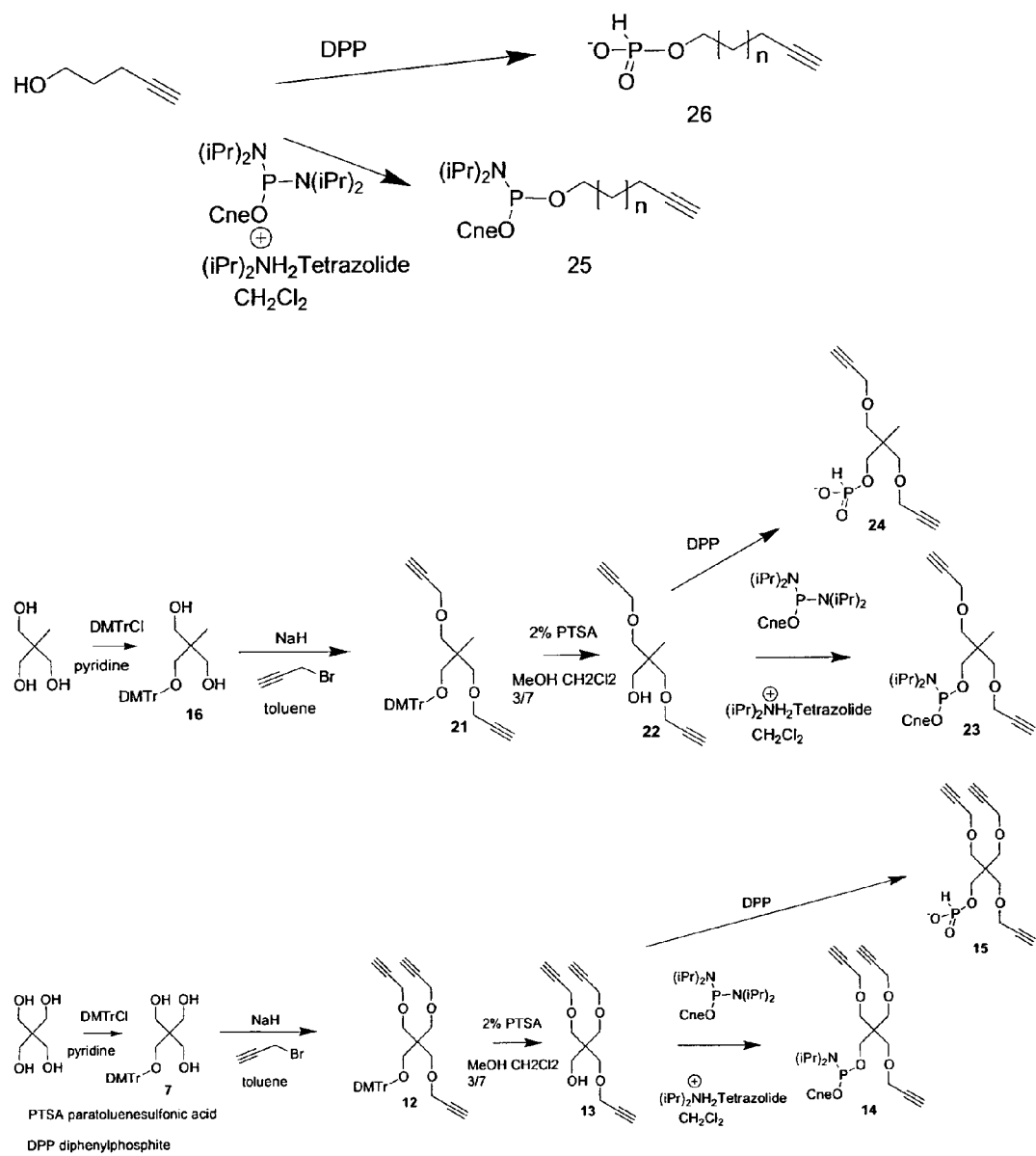

Figure 13: Synthesis of building blocks for introduction of one, two or three alkyne functions in an oligonucleotide.

Figure 14:
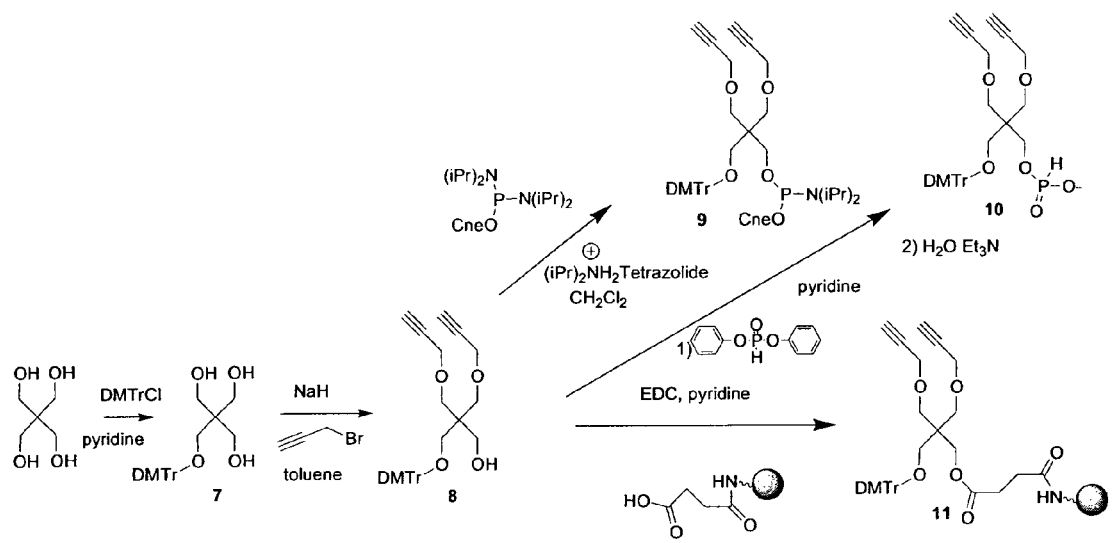

Figure 14: Synthesis of building blocks for introduction or two alkyne functions in an oligonucleotide.

Figure 15:
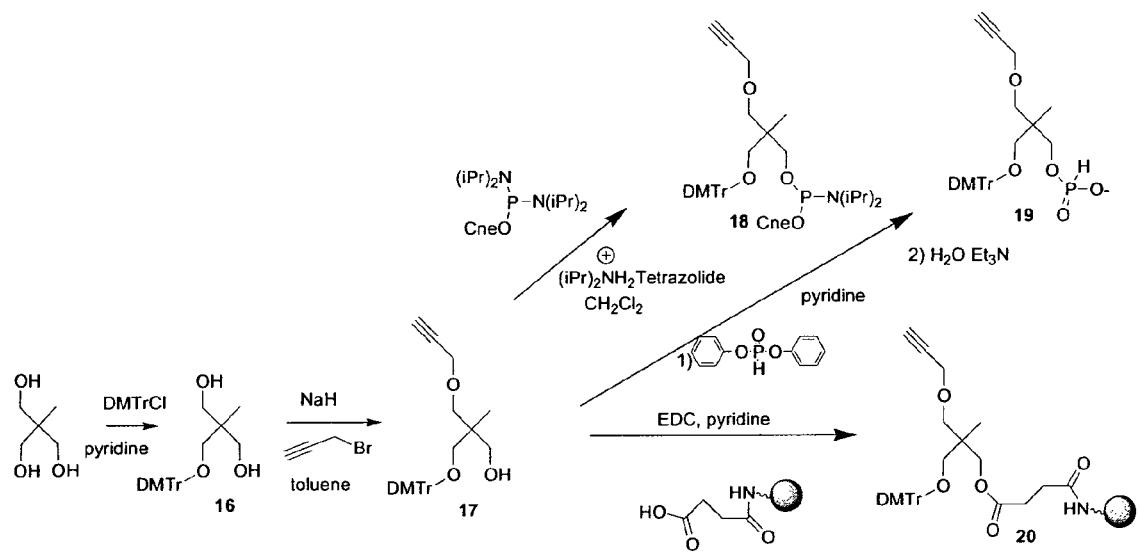

Figure 15: Synthesis of building blocks for introduction or one alkyne function in an oligonucleotide.

Figure 16:
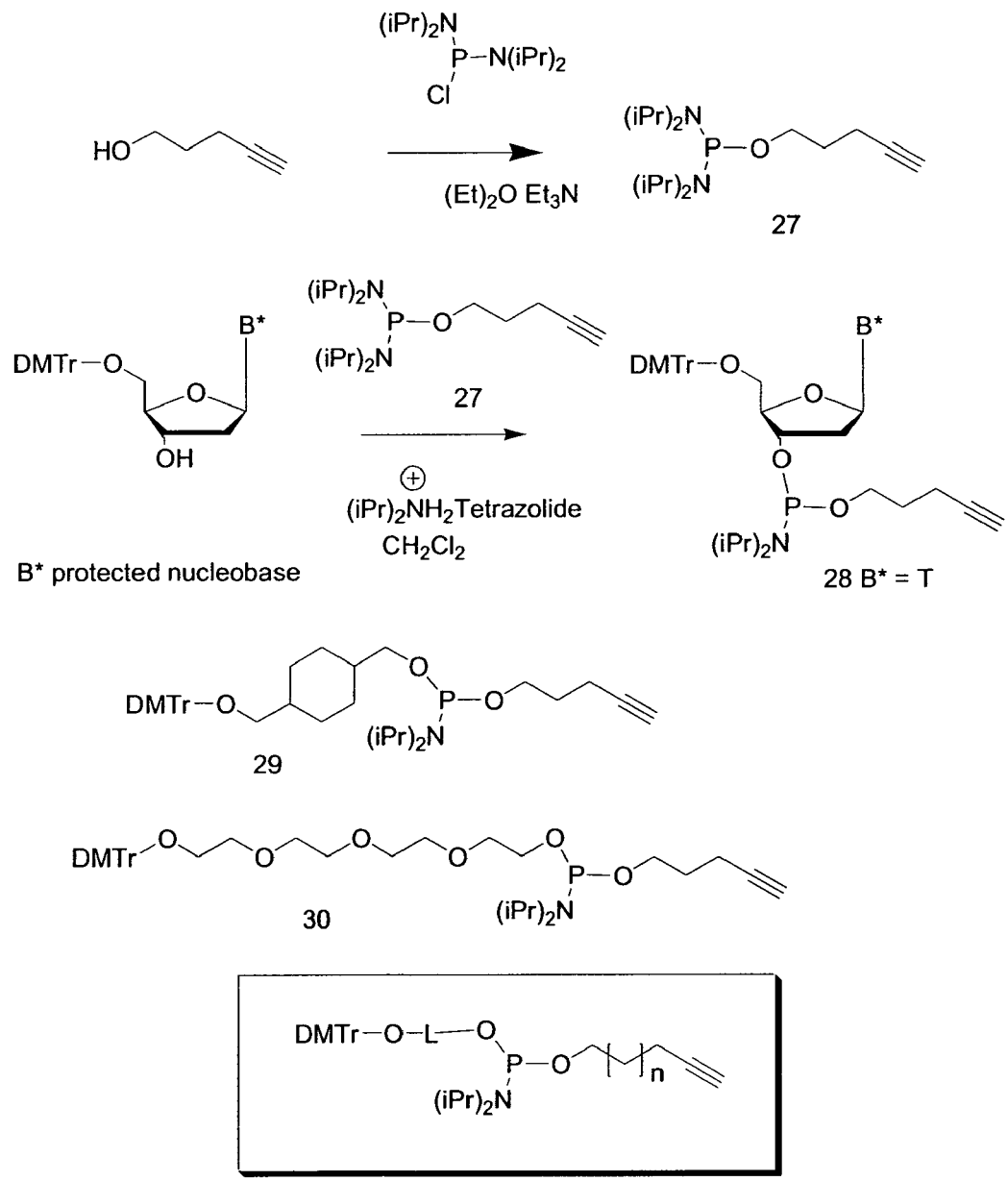

Figure 16: Synthesis of building blocks for introduction or one alkyne function in an oligonucleotide through a phosphotriester linkage.

Figure 17:
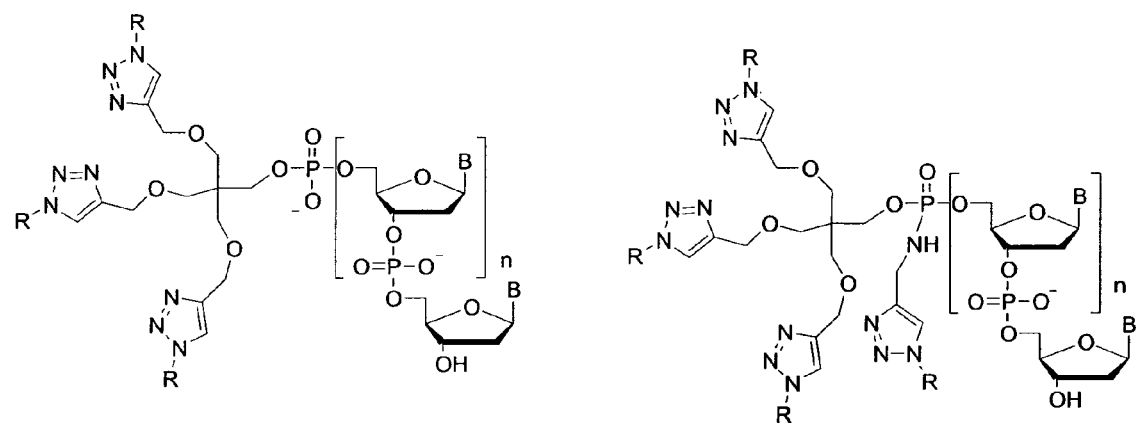

Figure 17: Examples of structures obtained after click chemistry from phosphodiester substituted by three alkyne functions and from a phosphoramidate bearing four alkyne functions

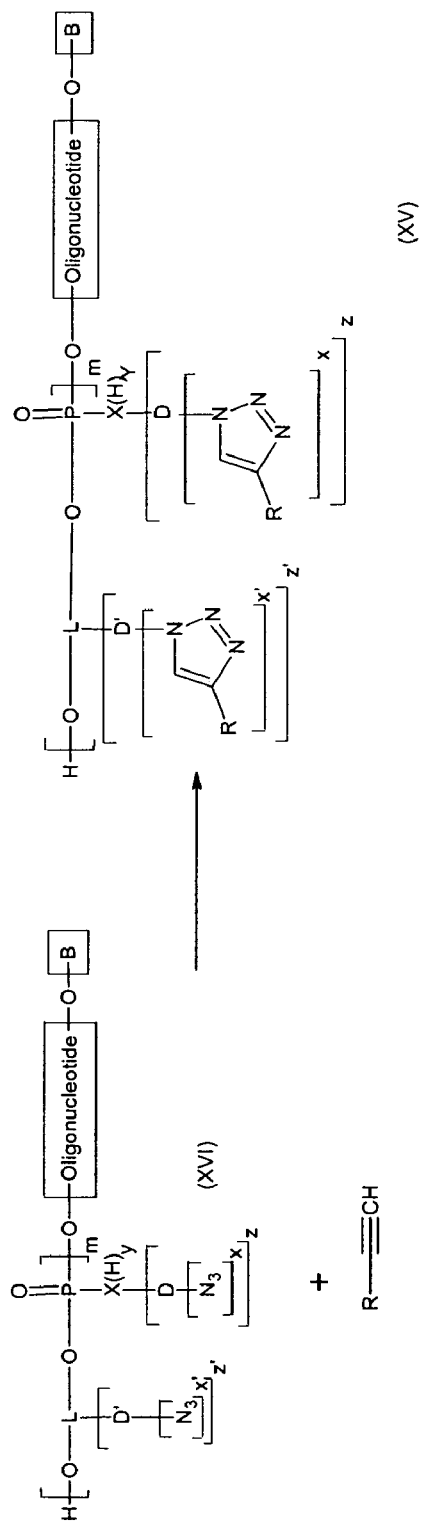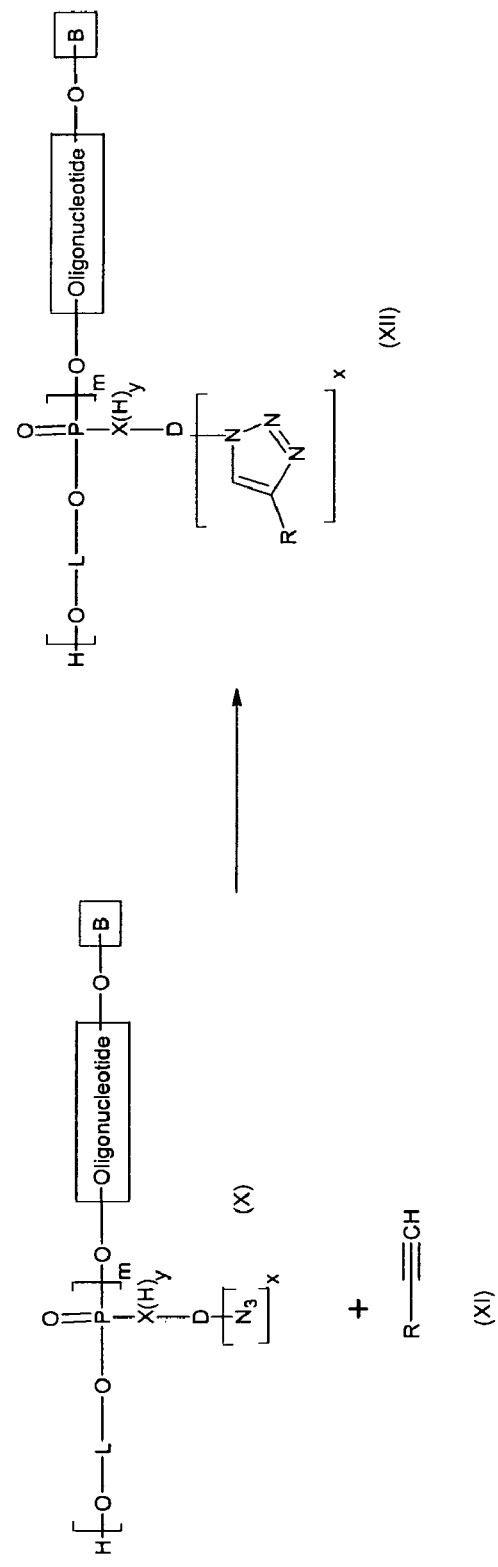
Figure 20A
Figure 20B

METHOD FOR THE SYNTHESIS OF OLIGONUCLEOTIDE DERIVATIVES

CROSS REFERENCE TO RELATED APPLICATIONS

This application is a national stage application filed under 35 U.S.C. 371 of International Application No. PCT/IB2007/002486, filed Apr. 26, 2007, which claims priority from U.S. Provisional Application No. 60/745,905, filed Apr. 28, 2006.

FIELD AND BACKGROUND OF THE INVENTION

The invention is directed to a method for the synthesis of nucleotide derivatives wherein molecules of interest are grafted on the oligonucleotide with the help of a "click chemistry" reaction between an azide function on the molecule of interest and an alkyne function on the oligonucleotide, or between an alkyne function on the molecule of interest and an azide function on the oligonucleotide.

Other objects of the invention are intermediate molecules, notably alkyne functionalized oligonucleotides, azide functionalized oligonucleotides, grafted oligonucleotides, oligonucleotide micro arrays containing them and the use of those grafted oligonucleotides for biological investigation and for cell targeting among others.

Oligonucleotides are molecules consisting of a short chain of nucleotides, the number of which can vary from one to around one hundred. They are important molecular tools for genomic research and biotechnology (Caruthers, M. H. *Science* 1985, 230, 281-285). Most applications require labeling with dyes or other biomolecules such as peptides (Zatsepin, T. S.; Turner, J. J.; Oretskaya, T. S.; Gait, M. J. *Curr. Pharm. Des.* 2005, 11, 3639-3654), or carbohydrates (Zatsepin, T. S.; Oretskaya, T. S. *Chem. Biodiversity* 2004, 1, 1401-1417).

Oligonucleotides are typically synthesized on solid support using phosphoramidite chemistry (Beaucage, S. L.; Caruthers, M. H. *Tetrahedron Lett.* 1981, 22, 1859-1862). Their conjugation with carbohydrates has been performed on one hand on solid support using either solid-supported carbohydrates (Adinolfi, M.; De Napoli, L.; Di Fabio, G.; Iadonisi, A.; Montesarchio, D.; Piccialli, G. *Tetrahedron* 2002, 58, 6697-6704; D'Onofrio, J.; de Champdore, M.; De Napoli, L.; Montesarchio, D.; Di Fabio, G. *Bioconjugate Chem.* 2005, 16, 1299-1309) or carbohydrate phosphoramidites (Adinolfi, M.; De Napoli, L.; Di Fabio, G.; Iadonisi, A.; Montesarchio, D.; Piccialli, G. *Tetrahedron* 2002, 58, 6697-6704; D'Onofrio, J.; de Champdore, M.; De Napoli, L.; Montesarchio, D.; Di Fabio, G. *Bioconjugate Chem.* 2005, 16, 1299-1309; Sheppard, T. L.; Wong, C. H.; Joyce, G. F. *Angew. Chem., Int. Ed.* 2000, 39, 3660-3663; Tona, R.; Bertolini, R.; Hunziker, J. *Org. Lett.* 2000, 2, 1693-1696; de Kort, M.; de Visser, P. C.; Kurzeck, J.; Meeuwenoord, N. J.; van der Marel, G. A.; Rüger, W.; van Boom, J. H. *Eur. J. Org. Chem.* 2001, 2075-2082; Dubber, M.; Frechet, J. M. *J. Bioconjugate Chem.* 2003, 14, 239-246), and on the other hand in solution using reactive carbohydrate derivatives (Akasaka, T.; Matsuura, K.; Emi, N.; Kobayashi, K. *Biochem. Biophys. Res. Commun.* 1999, 260, 323-328; Forget, D.; Renaudet, O.; Defrancq, E.; Dumy, P. *Tetrahedron Lett.* 2001, 42, 7829-7832; Dey, S.; Sheppard, T. L. *Org. Lett.* 2001, 3, 3983-3986). Nevertheless, these strategies require multi-step synthesis and are time consuming.

There remained the need for a method permitting the grafting of varied molecules of interest on an oligonucleotide backbone, with the possibility to graft several different molecules of interest on the oligonucleotide backbone, wherein said method permits the grafting of molecules of interest either on the 3'-, or on the 5'-extremity of the oligonucleotide, or inside the sequence.

The inventors have found that the use of a "click chemistry" reaction between an azide function on the molecule of interest and an alkyne function grafted on a phosphonate diester functionalization of the oligonucleotide permitted to reach this goal.

DETAILED DESCRIPTION

A first object of the invention is a method for the preparation of an oligonucleotide grafted by a molecule of interest R wherein said method comprises the step of reacting an azido function attached to R with an alkyne substituted phosphodiester derivative of the oligonucleotide, as depicted on FIGS. 1A and 1B.

On FIG. 1A, an oligonucleotide is grafted by a function responding to formula (Ia)

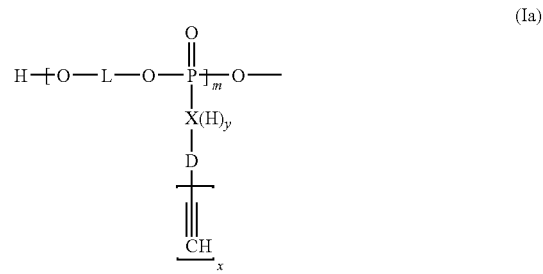

wherein X is selected from N, O, S, an alcane di-yl comprising 1 to 12 carbon atoms, like —$CH_2$—, —$CH_2$—$CH_2$— ...; preferentially X is selected from N, O;

m is an integer, $m \geq 1$

L is a linker which may be selected from the following list: alcane di-yl functions with 1 to 12 carbon atoms, linear branched or cyclic possibly interrupted by one or several oxygen (—O—), nitrogen (—NH—, —N=) or sulphur (—S—) bridges or phosphodiester [—O—($O^-$)P(=O)—O—] bridges;

x is an integer, $30 \geq x \geq 1$

Figure 12:
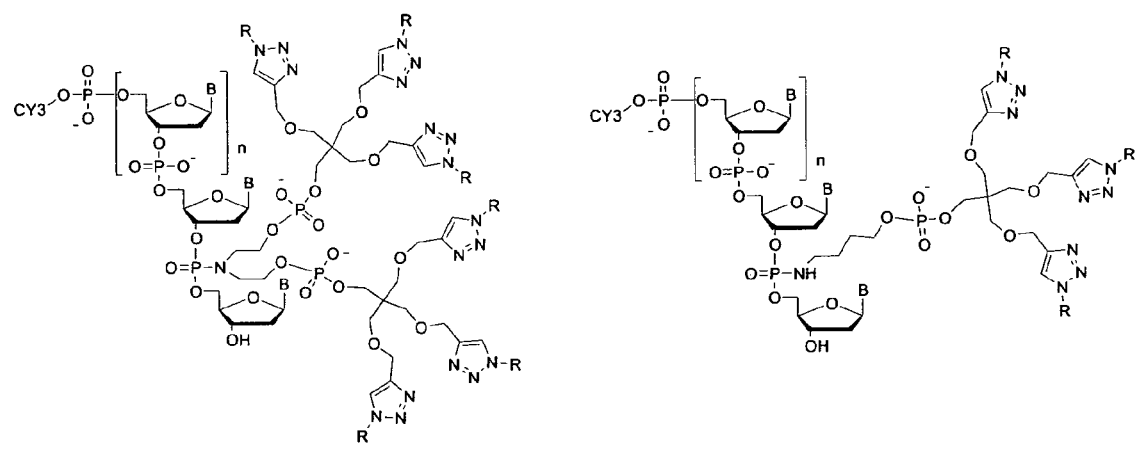

D is a linker between X and the alkyne group(s). According to the value of x, D's valency is 2 or more. Preferably, D is selected from alcane poly-yl groups comprising 1 to 36 carbon atoms, possibly interrupted by one or several oxygen (—O—), nitrogen (—NH—, —N=) or sulphur (—S—) bridges or phosphodiester [—O—($O^-$)P(=O)—O—] bridges. (FIG. 12)

According to the choice of X and D, y is 0, 1 or 2;

In formula (I) and (III) B is selected from H, a solid support (array, polymer, beads) or a tag.

On FIG. 1B, an oligonucleotide is grafted by a function responding to formula (Ib)

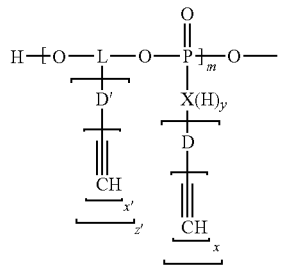

(Ib)

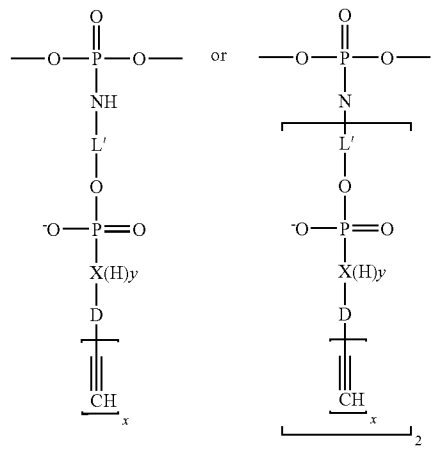

wherein X is selected from N, O, S, an alcane di-yl comprising 1 to 12 carbon atoms, like —$CH_2$—, —$CH_2$—$CH_2$— . . . ; preferentially X is selected from N, O;

m is an integer, m≧1

L is a linker which may be selected from the following list: alcane poly-yl functions with 1 to 12 carbon atoms, linear branched or cyclic possibly interrupted by one or several oxygen (—O—), nitrogen (—NH—, —N=) or sulphur (—S—) bridges or phosphodiester [—O—($O^-$)P(=O)—O—] bridges;

x is an integer, 30≧x≧1 x' is an integer, 30≧x'≧1

D is a linker between X and the alkyne group(s). According to the value of x, D's valency is 2 or more. Preferably, D is selected from alcane poly-yl groups comprising 1 to 36 carbon atoms, possibly interrupted by one or several oxygen (—O—), nitrogen (—NH—, —N=) or sulphur (—S—) bridges or phosphodiester [—O—($O^-$)P(=O)—O—] bridges;

D' is a linker between L and the alkyne group(s). According to the value of x', D''s valency is 2 or more. Preferably, D' is selected from alcane poly-yl groups comprising 1 to 36 carbon atoms, possibly interrupted by one or several oxygen (—O—), nitrogen (—NH—, —N=) or sulphur (—S—) bridges or phosphodiester [—O—($O^-$)P(=O)—O—] bridges;

z and z' are integers, z and z'≧0, at least one of z and z' is ≧1;

According to the choice of X and D, y is 0, 1 or 2;

In formula (I), (III), (XIII) and (XIV) B is selected from H, a solid support (array, polymer, beads) or a tag.

On formula (I) of FIG. 1A and (XIV) of FIG. 1B, the oligonucleotide is substituted by the function (Ia), respectively (Ib), either on its 3'-extremity, on its 5'-extremity or inside of the sequence, one P atom of the function (Ia) or (Ib) being part of the oligonucleotide chain. According to a variant illustrated on FIG. 12, the oligonucleotide of formula (I) or (XIV) can be an oligonucleotide derivative wherein one or several phosphate function(s) of the oligonucleotide chain has been replaced by a phosphoramidate group of the type:

in which L' is an alcane di-yl chain comprising 1 to 12 carbon atoms.

In that case, the P atom of the phosphodiester group in the (Ia) or (Ib) formula is not part of the oligonucleotide chain, but is linked to the oligonucleotide chain through a P—NH-L'-O—P link. The grafted nucleotide of formula (I) or (XIV) can be in solution (case when B=H or a tag), or it can comprise a grafting to a solid support by one of its extremities (case when B=solid support).

The molecule of interest R is grafted by an azido function.

When the azido-functionalized molecule of interest (II) is contacted with the oligonucleotide derivative (I) or (XIV) in appropriate quantity, a 1,3-dipolar cycloaddition occurs leading to the triazole (III), respectively (XIII).

This 1,3-dipolar cycloaddition is very chemoselective, only occurring between alkynyl and azido functional groups with high yields. The resulting 1,2,3-triazoles are stable at high temperature and in aqueous conditions.

The molecule of interest can be any molecule for which there is an interest at obtaining a condensation product with an oligonucleotide. For the sake of illustration, mention may be made of: carbohydrates, peptides, lipids, oligonucleotides, biotin, ferrocenyl compounds, fluorescent tags . . . .

Favourite molecules of interest are carbohydrates, including their various derivatives. The importance of oligonucleotide-carbohydrate conjugates has been highlighted by T. S. Zatsepin and T. S. Oretskaya in *Chemistry and Biodiversity*, vol. 1 (2004), 1401-1417. This review also highlights the difficulties associated to their preparation and lists the few methods known for this purpose.

Carbohydrates include mono and polysaccharides and their derivatives. As monosaccharides and their derivatives, mention may be made of glucose, fructose, mannose, ribose, glyceraldehyde, ribose, erythrose, threose, xylose, arabinose, lyxose, ribulose, xylulose, allose, altrose, gulose, idose, lactose, galactose, talose, sorbose, tagatose, psicose, dihydroxy acetone, glucosamine, N'-acetylglucosamine, glucuronic acid, sialic acid . . . .

Polysaccharides can be built by any combination of monosaccharides and monosaccharide derivatives, either identical or different, in a linear or branched assembly.

Particularly preferred are molecules (II) consisting of a mono or a polysaccharide grafted on one of its extremities by a —$CH_2$—($CH_2$—O—$CH_2$)$_r$—$CH_2$—$N_3$ group, with r an integer, r≧1, r=1, 2, 3, 4, 5, 6, . . . .

Figure 18:
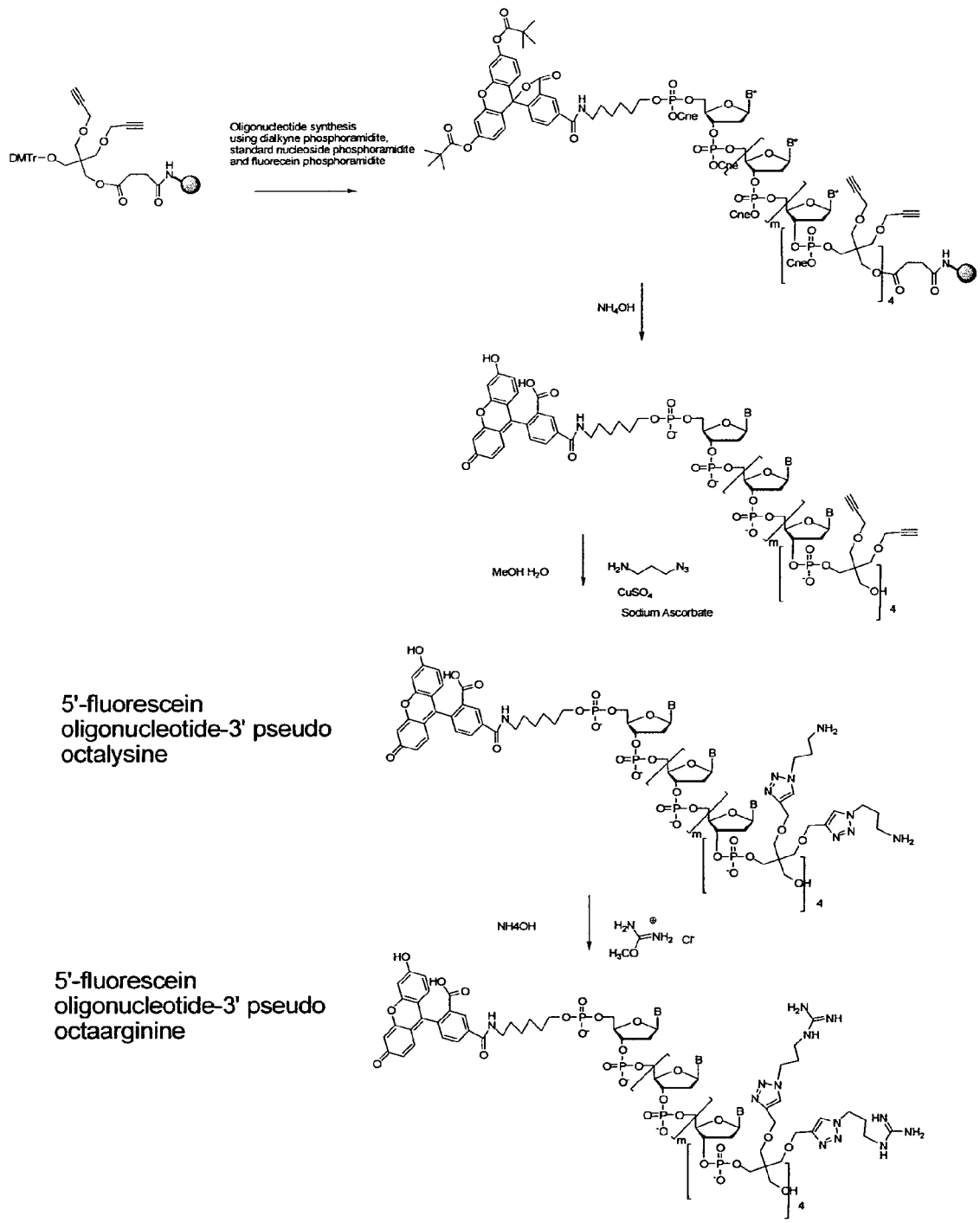

Another type of favourite molecules of interest R consists of amino acids and peptides. Tags, like fluorescent tags notably are also favorite molecules of interest that one can graft on the oligonucleotide chain, by using the method of the invention. Such variants are illustrated on FIG. 18. On this figure is illustrated the preparation of an oligonucleotide comprising m+2 nucleotide units, the 5'-extremity being grafted by a fluorescein and the 3'-extremity bearing a phosphate di-ester chain of four units, each unit being substituted by a linker arm bearing two guanidine residues.

Figure 2:
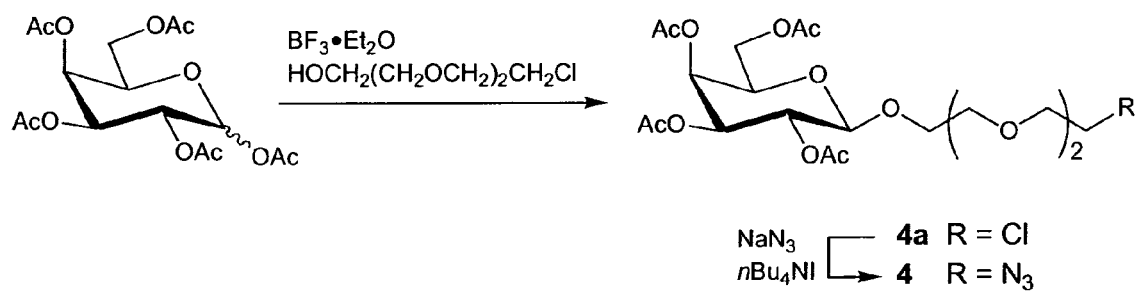

Preparation of Molecules (II) can be Performed According to the Scheme illustrated on FIG. 2 in the case of galactose.

Penta-O-acetyl galactopyrranosyl is reacted with HOCH$_2$(CH$_2$OCH$_2$)$_r$CH$_2$Cl, wherein r is an integer, r≧1 (here r=2), in the presence of BF$_3$ in diethylether. Then a treatment of the resulting chloride with NaN$_3$ and nBu$_4$Ni gives the expected azido derivative. The choice of reactive illustrated in FIG. 2 is not limiting, HOCH$_2$(CH$_2$OCH$_2$)$_r$CH$_2$OTs or HOCH$_2$(CH$_2$OCH$_2$)$_r$CH$_2$I could be used instead of HOCH$_2$(CH$_2$OCH$_2$)$_r$CH$_2$Cl.

This method is given for the purpose of illustration. Any other known method for preparing azido derivatives is acceptable. A list of such reactions is given in Advanced Organic Chemistry, J. March, Wiley, 1985, p. 1155.

With regards to the conditions for reacting the azide derivative (II) with the oligonucleotide (I) or (XIV) as illustrated on FIGS. 1A and 1B, the favourite conditions are the following.

The molecule (II) is in solution in an appropriate solvent (water and/or organic) and the molecule (I) or (XIV) is either in solution or grafted onto a solid support (resin or glass or silicon for example). Preferentially the reaction is made with application of microwaves.

Microwave activation significantly improves the reaction kinetic. Heating at a temperature superior to room temperature also has a positive effect on the reaction kinetic. Preferentially the reactive medium is heated to a temperature comprised between 30 and 100° C. However, at room temperature the reaction occurs also.

The reaction is performed with the presence of a Copper (Cu$^+$) catalyst that could be for example generated by CuSO$_4$ and sodium ascorbate.

Molecules of formula (XIV) and (I), which are a particular variant of molecules (XIV), are key intermediates in the method which has been described above. As such they are another object of the invention.

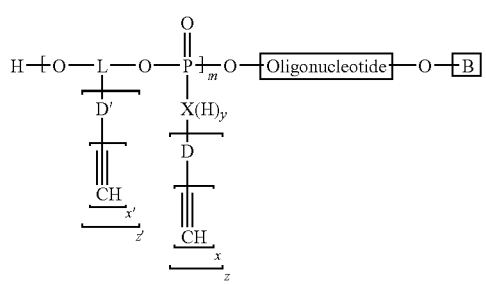

(XIV)

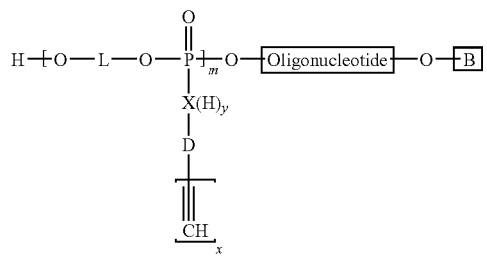

(I)

The variables in formula (I) and (XIV) are the same as defined above:

X is selected from N, O, S, an alcane di-yl comprising 1 to 12 carbon atoms, like —CH$_2$—, —CH$_2$—CH$_2$— . . . ; preferentially X is selected from N, O;

m is an integer, m≧1

L is a linker which may be selected from the following list: alcane poly-yl functions with 1 to 12 carbon atoms, linear branched or cyclic possibly interrupted by one or several oxygen (—O—), nitrogen (—NH—, —N═) or sulphur (—S—) bridges or phosphodiester [—O—(O$^-$)P(═O)—O—] bridges;

x is an integer, 30≧x≧1; in (I) L is selected from alcane di-yl radicals with 1 to 12 carbon atoms, linear branched or cyclic possibly interrupted by one or several oxygen (—O—), nitrogen (—NH—, —N═) or sulphur (—S—) bridges or phosphodiester [—O—(O$^-$)P(═O)—O—] bridges;

x' is an integer, 30≧x'≧1

D is a linker between X and the alkyne group(s). According to the value of x, D's valency is 2 or more. Preferably, D is selected from alcane poly-yl groups comprising 1 to 36 carbon atoms, possibly interrupted by one or several oxygen (—O—), nitrogen (—NH—, —N═) or sulphur (—S—) bridges or phosphodiester [—O—(O$^-$)P(═O)—O—] bridges;

D' is a linker between L and the alkyne group(s). According to the value of x', D''s valency is 2 or more. Preferably, D' is selected from alcane poly-yl groups comprising 1 to 36 carbon atoms, possibly interrupted by one or several oxygen (—O—), nitrogen (—NH—, —N═) or sulphur (—S—) bridges or phosphodiester [—O—(O$^-$)P(═O)—O—] bridges;

z and z' are integers, z and z'≧0, at least one of z and z' is ≧1;

The oligonucleotide can be a nucleotide chain comprising 1 to 100 nucleotide units, the chain of formula (Ia) or (Ib) being grafted on its 3'-extremity, on its 5'-extremity or inside of the sequence, one P atom of the function (Ia) or (Ib) being part of the oligonucleotide chain. According to a variant illustrated on FIG. 12, the oligonucleotide of formula (I) or (XIV) can be an oligonucleotide derivative wherein one or several phosphate function(s) of the oligonucleotide chain has been replaced by a phosphoramidate group of the type:

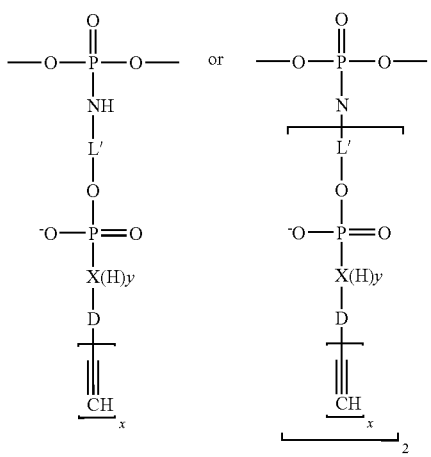

in which L' is an alcane di-yl chain comprising 1 to 12 carbon atoms. In that case, the P atom of the phosphodiester group in the (Ia) or (Ib) function is not part of the oligonucleotide chain, but is linked to the oligonucleotide chain through a P—NH-L'-O—P link.

According to the choice of X and D, y is 0, 1 or 2;

In formula (I), (III), (XIV) and (XIII) B is selected from H, a solid support (array, polymer, beads) or a tag.

Particularly, in molecules of formula (I) and (XIV), favourite variants are the following:

m is an integer selected from 1, 2, 3, 4, 5, 6.
L is a linker selected from:
an alcane poly-yl (di-yl for (I)) with 1 to 12 carbon atoms, linear, branched or cyclic;
a group

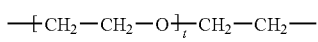

with t an integer selected from 1, 2, 3, 4, 5, 6;
an alcane poly-yl (di-yl for (I)) with 1 to 12 carbon atoms including an oxygen comprising heterocycle, like a ribose cycle;
D is an alcane poly-yl group comprising 1 to 12 carbon atoms possibly interrupted by one or several oxygen bridges.

Examples of linkers are given here-under for the purpose of illustration.

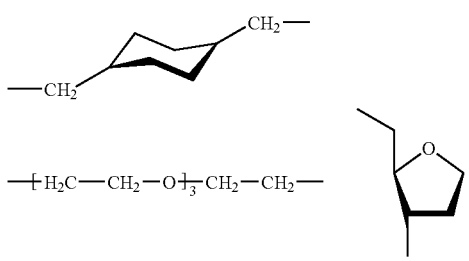

According to the linker's length, the distance between the molecules of interest will be modulated.

D can be divalent like an alcane di-yl comprising 1 to 12 carbon atoms. For example D can be —CH$_2$—.

D can have a higher valency and create a link between the nitrogen and several alkyne functions so that a dendrimer can be built.

As an illustrative example of this case,

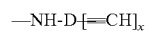

can be:

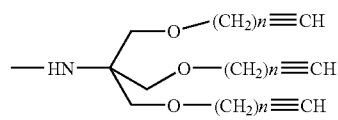

with n an integer n≧1, like for example:

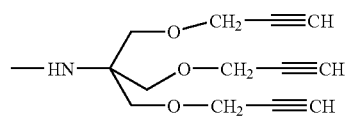

Another possibility for obtaining a multifunctional compound is to have the amine substituted twice by an alkyne bearing linker.

For example

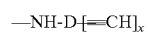

can be:

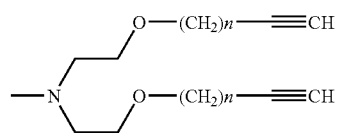

with n an integer n≧1, like for example:

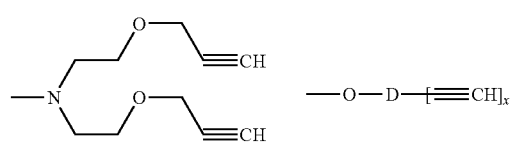

can be:

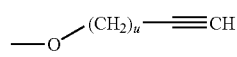

with u an integer

All combinations of the illustrated variants are possible.

Methods for the introduction of one, two or three alkyne functions on the phosphoester or phosphoramidate function are illustrated on FIGS. 13, 14, 15 and 16. Examples of molecules of formula (III) and (XIII) obtained from a phosphodiester comprising three alkyne functions, or a phosphoramidate comprising four alkyne functions, are illustrated on FIG. 17.

B can be H or a tag or a resin or a glass or silicon plaque, a bead, a polymer.

The reaction depicted on FIGS. 1A and 1B can be performed with B=H or B=tag or B=a solid support.

If it is performed with B=a solid support, and if desired, the resulting product (III) or (XIII) can then be detached from the solid support with an appropriate treatment.

When R is a carbohydrate or a carbohydrate derivative, the reaction depicted on FIG. 1A or 1B is done with an appropriate protection on R's hydroxyl functions. This protection can be removed after the 1,3-cycloaddition has been performed.

Figure 3:
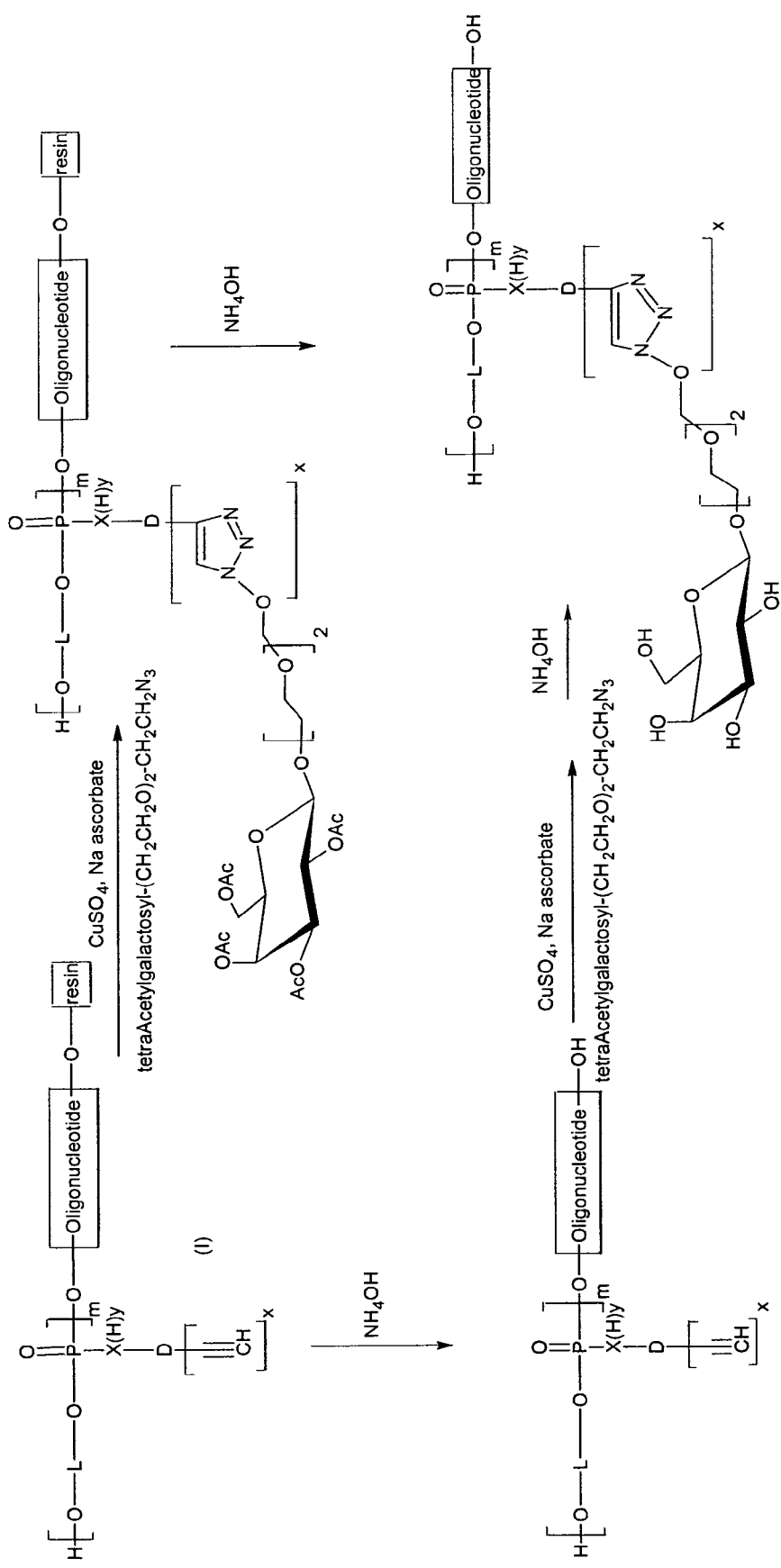

Variants of this type are illustrated on FIG. 3, in the case when the molecule of interest is tetra acetyl galactosyl.

A molecular array comprising an oligonucleotide-grafted solid support (glass, silicon, polymer or resin) to which molecules (Ia) or (Ib) are hybridized, directly to the oligonucleotides or through a linker arm, is another object of the invention. It corresponds to molecule (I) and (XIV) when B is a solid support.

The Huisgen's 1,3-dipolar cyclo addition between alkyne and azide is very attractive since it is nearly quantitative, can be performed in water with an organic co-solvent and multiple cycloadditions can be performed on multivalent scaffolds (Wang, Q.; Chan, T. R.; Hilgraf, R.; Fokin, V. V.; Sharpless, K. B.; Finn, M. G. *J. Am. Chem. Soc.* 2003, 125, 3192-3193). Furthermore, this reaction is orthogonal to most typical organic transformations and therefore highly chemoselective.

"Click chemistry" has been successfully applied for fluorescent labeling of oligonucleotides in solution (Seo, T. S.; Li, Z.; Ruparel, H.; Ju, J. *J. Org. Chem.* 2003, 68, 609-612) and recently for the attachment of an oligonucleotide on a monolayer (Devaraj, N. K.; Miller, G. P.; Ebina, W.; Kakaradov, B.; Collman, J. P.; Kool, E. T.; Chidsey, C. E. D. *J. Am. Chem. Soc.* 2005, 127, 8600-8601) and for DNA metallization (Burley, G. A.; Gierlich, J.; Mofid, M. R.; Nir, H.; Tal, S.; Eichen, Y.; Carell, T. *J. Am. Chem. Soc.* 2006, 128, 1398-1399).

However prior art "click chemistry" applied to oligonucleotides used azido functionalized oligonucleotides in which only one azido function could be introduced at the 5' extremity of the oligonucleotide, or alkyne phosphoramidite oligonucleotides or nucleotides substituted on their basic ring by an alkyne radical.

Nowhere in the prior art is mentioned or suggested to use alkyne phosphoester derivatives of the oligonucleotides to make the 1,3-cyclo addition with an azide substituted molecule of interest. Neither is it taught or suggested to use azide phosphoester derivatives of the oligonucleotides to make the 1,3-cyclo addition with an alkyne substituted molecule of interest This method is extremely efficient for the synthesis of substituted oligonucleotides with a substitution at the 3'-extremity, the 5'-extremity or inside of the sequence itself.

In the case of a 3'-substituted oligonucleotide of formula (XIV) or (I), the reaction with the azido substituted molecule of interest (II) can be followed by another step of oligonucleotide synthesis, so that other nucleotide units are added to the chain, and alkyne functionalization can be performed on those units, so that another, and possibly a different azido substituted molecule of interest can be grafted on the oligonucleotide chain.

Figure 4:
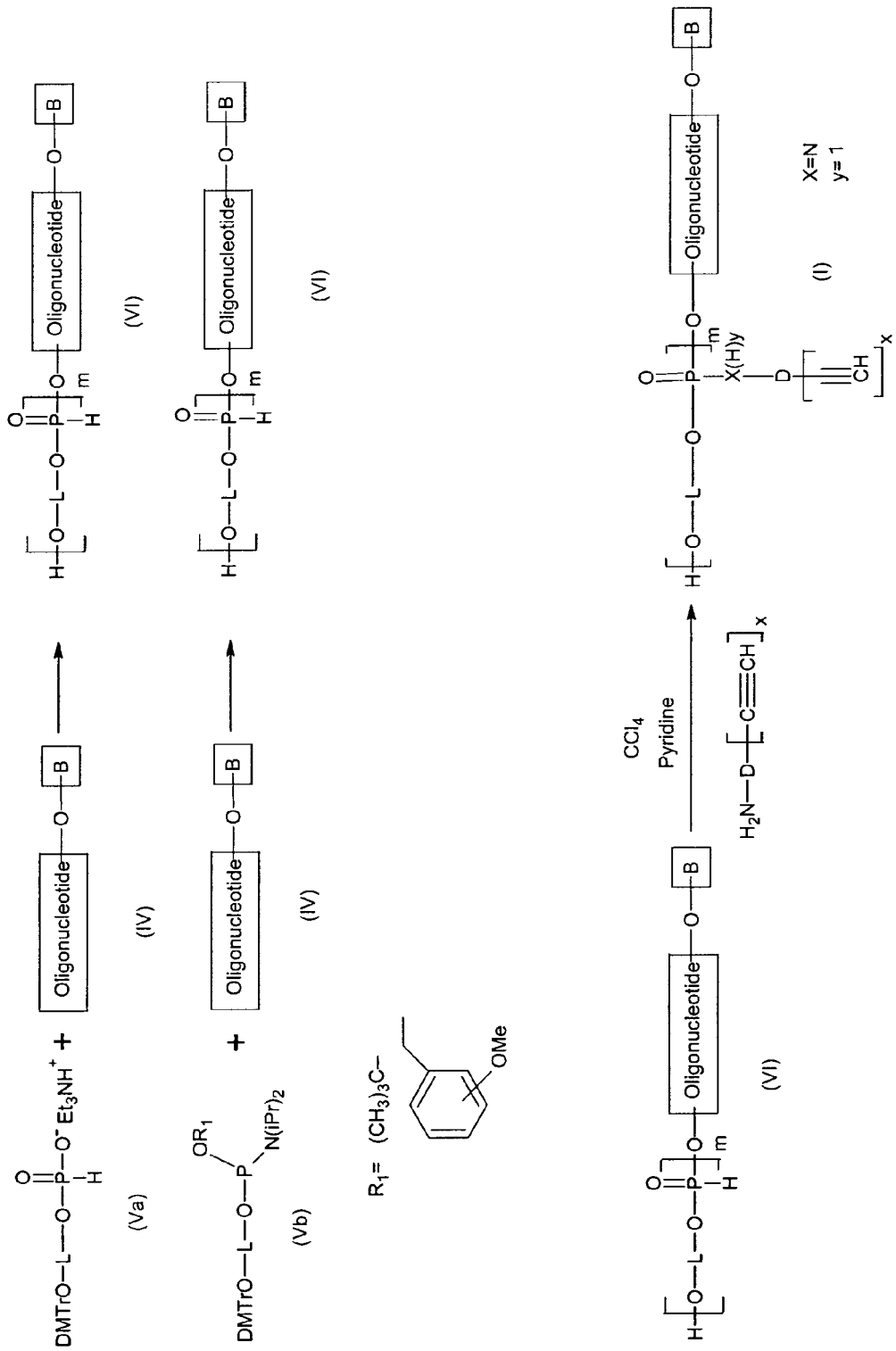

According to the invention when X=N the molecule of formula (XIV), especially (I), can be prepared by a method comprising the following steps and depicted on FIG. 4.

A phosphonate (Va) or a phosphoramidite (Vb) is reacted with an oligonucleotide (IV) on its 3' or 5' extremity or inside of the sequence, giving a hydrogeno-phosphonate diester (IV), wherein L, m, B have the same meaning as above.

Such Arbuzov, or Arbuzov-like, reactions have been disclosed in Meyer A. et al., *Tetrahedron Letters,* 2004, 45(19), 3745-3748 and Ferreira F. et al., *Journal of Organic Chemistry,* 2005, 70(23), 9198-9206.

Then in a second step compound (VI) is treated by carbon tetrachloride in the presence of an alkyne amine to give the phosphoramidate (I).

Figure 5:
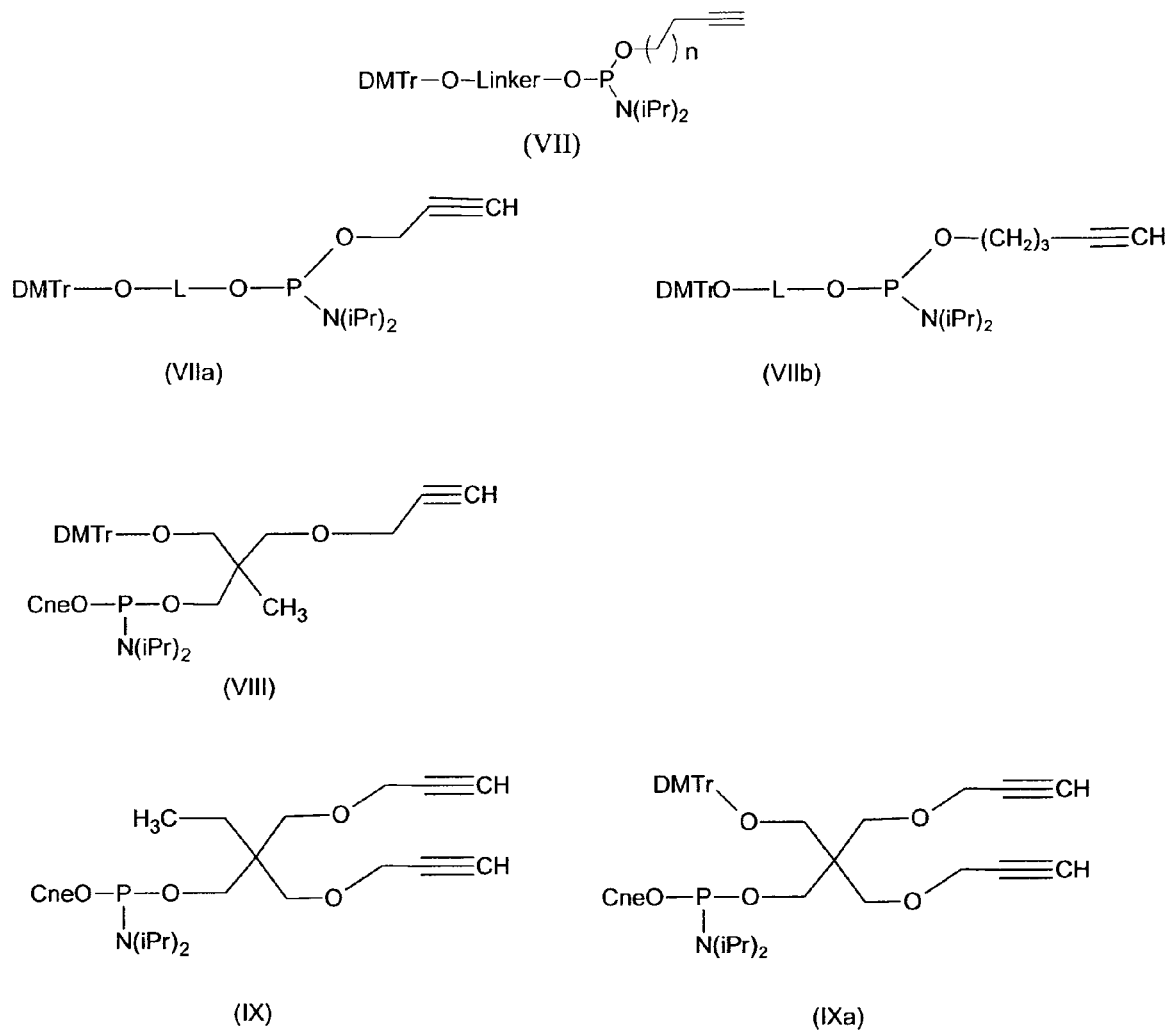

According to a variant of the invention when X=O the molecule of formula (XIV), especially (I) can be prepared by a method comprising the following steps:

A phosphoramidite of formula (VII), especially (VIIa) and (VIIb), or (VIII), (IX) or (IXa) (FIG. 5) is reacted with the oligonucleotide (IV) to give directly the molecule (I).

Molecules of formula (XIII) and (III) as above disclosed are another object of the invention.

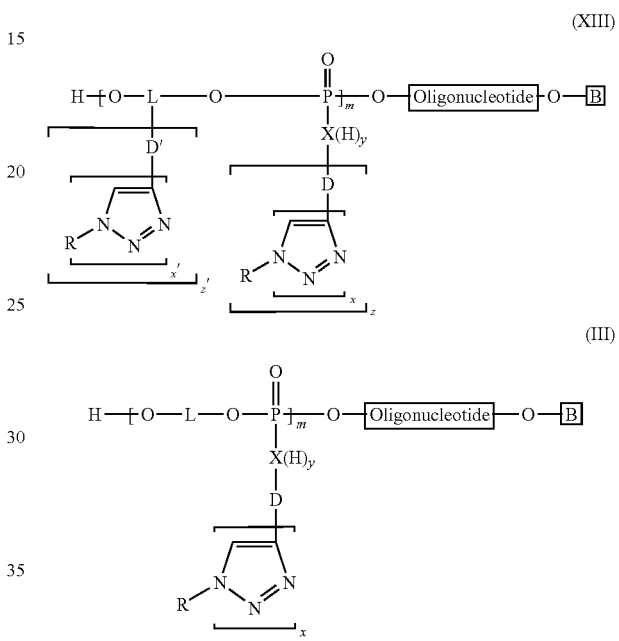

They comprise an oligonucleotide chain with at least one phosphodiester chain substitution on one of their extremities or in the chain sequence itself with one or several molecules of interest R grafted on the phosphonate group through a triazole intermediate group. They may be attached to a solid support or they can be in solution. In one molecule of formula (XIII) or (III), the different R substituents can be identical or different all along the phosphodiester chain. Preferentially R is a carbohydrate derivative, particularly preferred are molecules wherein R consists of a mono or a polysaccharide grafted on one of its extremities by a —$CH_2$—($CH_2$—O—$CH_2$)$_r$—$CH_2$— groups, with r an integer, r=1, 2, 3, 4, 5, 6, . . . .

In formula (XIII) and (III), X is selected from N, O, S, an alcane di-yl comprising 1 to 12 carbon atoms, like —$CH_2$—, —$CH_2$—$CH_2$— . . . ; preferentially X is selected from N, O; m is an integer, m≧1

L is a linker which may be selected from the following list: alcane poly-yl functions with 1 to 12 carbon atoms, linear branched or cyclic possibly interrupted by one or several oxygen (—O—), nitrogen (—NH—, —N=) or sulphur (—S—) bridges or phosphodiester [—O—(O⁻)P(=O)—O—] bridges; in (III) L is an alcane di-yl radical with 1 to 12 carbon atoms, linear branched or cyclic possibly interrupted by one or several oxygen (—O—), nitrogen (—NH—, —N=) or sulphur (—S—) bridges or phosphodiester [—O—(O⁻)P(=O)—O—] bridges;

x is an integer, 30≧x≧1 x' is an integer, 30≧x'≧1

D is a linker between X and the carbon in position 4 of the triazole ring(s). According to the value of x, D's valency is 2 or more. Preferably D is selected from alcane poly-yl groups comprising 1 to 36 carbon atoms, possibly interrupted by one or several oxygen (—O—), nitrogen (—NH—, —N=) or sulphur (—S—) bridges or phosphodiester [—O—(O⁻)P(=O)—O—] bridges.

According to the choice of X and D, y is 0, 1 or 2;

D' is a linker between L and the carbon in position 4 of the triazole ring(s). According to the value of x', D''s valency is 2 or more. Preferably D' is selected from alcane poly-yl groups comprising 1 to 36 carbon atoms, possibly interrupted by one or several oxygen (—O—), nitrogen (—NH—, —N=) or sulphur (—S—) bridges or phosphodiester [—O—(O⁻)P(=O)—O—] bridges.

z and z' are integers, z and z'≧0, at least one of z and z' is ≧1;

In formula (XIII)) and (III) B is selected from H, a solid support (array, polymer, beads) or a tag.

The oligonucleotide can be a nucleotide chain comprising 1 to 100 nucleotide units, the chain of formula (Ia) or (Ib) being grafted on its 3'-extremity, on its 5'-extremity or inside of the sequence, one P atom of the function (Ia) or (Ib) being part of the oligonucleotide chain. According to a variant illustrated on FIG. 12, the oligonucleotide of formula (III) or (XIII) can be an oligonucleotide derivative wherein one or several phosphate function(s) of the oligonucleotide chain has been replaced by a phosphoramidate group of the type:

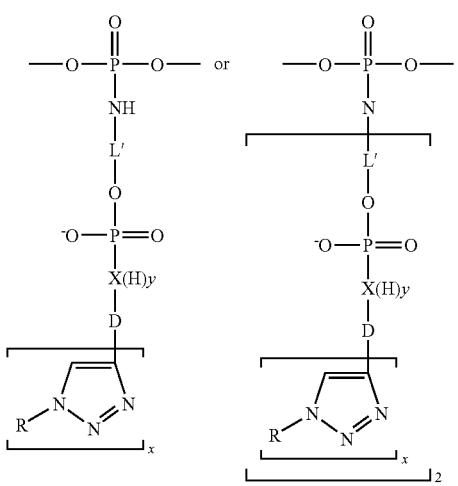

in which L' is an alcane di-yl chain comprising 1 to 12 carbon atoms. In that case, the P atom of the phosphodiester group is not part of the oligonucleotide chain, but is linked to the oligonucleotide chain through a P—NH-L'-O—P link.

The grafted nucleotide of formula (XIII) and (III) can be in solution (case when B=H or a tag), or it can be grafted to a solid support by one of its extremities (case when B=solid support).

Particularly, in molecules of formula (XIII) and (III), favourite variants are the following:

m is an integer selected from 1, 2, 3, 4, 5, 6.

L is a linker selected from:

an alcane poly-yl (di-yl in (III)) with 1 to 12 carbon atoms, linear, branched or cyclic;

a group

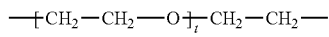

with t an integer selected from 1, 2, 3, 4, 5, 6;

an alcane poly-yl (di-yl in (III)) with 1 to 12 carbon atoms including an oxygen comprising heterocycle, like a ribose cycle;

D is an alcane poly-yl group comprising 1 to 12 carbon atoms possibly interrupted by one or several oxygen bridges.

Other known substituents can be added to this structure, like fluorescent groups which are generally introduced on the 5'-extremity of the oligonucleotide chain in a known manner.

Another object of the invention is a molecular array of formula (XIII), especially (III) consisting of a solid support grafted by a molecule as depicted above in formula (XIII) and (III) in a covalent or non covalent manner.

Figure 6:
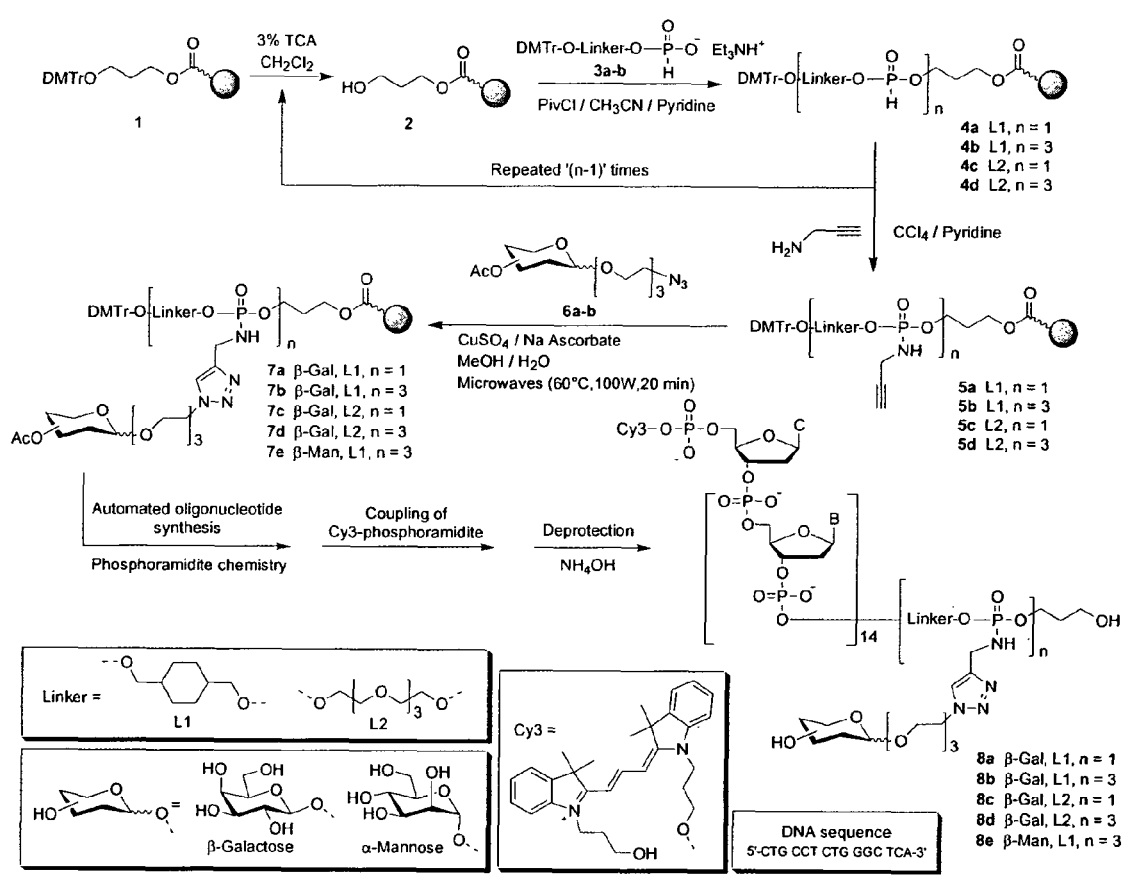

FIG. 6 illustrates the method for the preparation of a 3'-substituted oligonucleotide according to the invention. According to said method a sequence of m linker grafted phosphonates is attached to a resin or any solid support by the successive addition of m linker phosphonate groups. Reaction with carbon tetra chloride and propargylamine gives the corresponding phosphoramidate and 1,3-cycloaddition of the alkyne function with azido grafted carbohydrate gives the corresponding triazole. Then supported synthesis of oligonucleotides and coupling with the phosphoramidite method gives the 3'-substituted oligonucleotide.

Repetition of this method with three different carbohydrates gave access to the molecules illustrated in FIG. 7.

Figure 19:
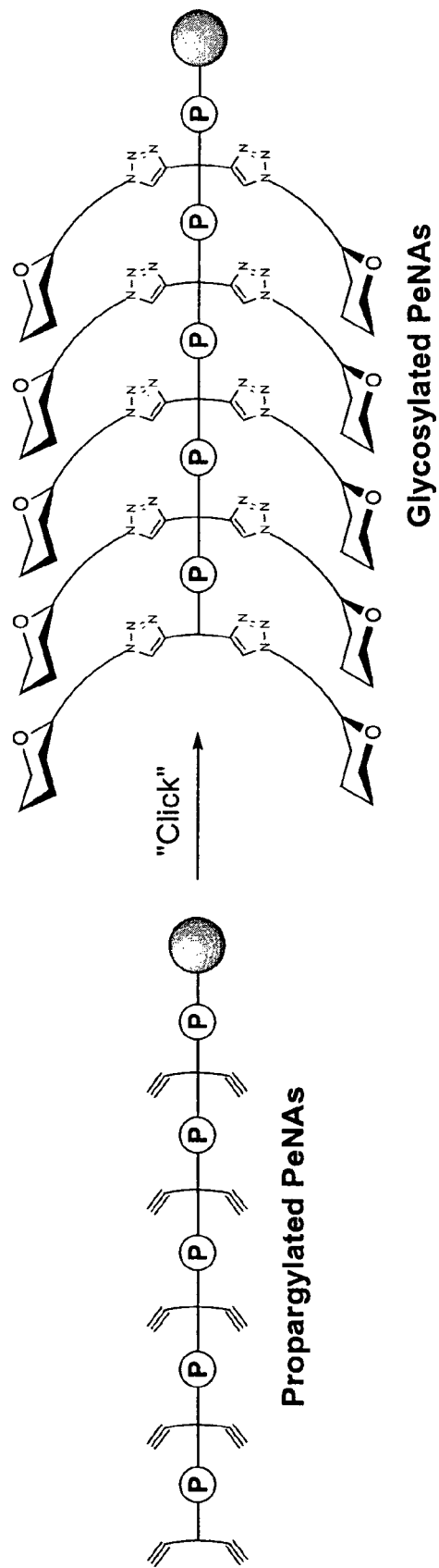

The variant of FIG. 19 illustrates a molecule of formula (XIV) and a molecule of formula (XIII) wherein one nucleotide bears a phosphodiester chain (case wherein z=0 and z'=1).

FIG. 19 presents a flexible synthetic approach to afford rapidly and easily Pentaerythrityl Nucleic Acids (PeNAs) based on a bis-2,2-saccharidyl-1,3-propanediol phosphodiester scaffold. Their synthesis was based on a combination of oligonucleotide phosphoramidite chemistry on solid support and microwave assisted click chemistry. The PeNAs were incorporating only one nucleotide at the pseudo-3'-end as a tag for the determination of glycosylated PeNAs concentration by UV analysis. The propargylated PeNAs were conveniently prepared using a phosphoramidite dialkyne building block which was coupled several times using a DNA-like synthesis on solid support.

Another object of the invention is a method for the preparation of an oligonucleotide grafted by a molecule of interest R wherein said method comprises the step of reacting an alkyne function attached to R with an azido substituted phosphodiester derivative of the oligonucleotide, as depicted on FIGS. 20A and 20B.

On FIG. 20A, the molecule of formula (XVI) is reacted with an alkyne functionalized molecule of interest (XI) to give the molecule (XV) by a click chemistry reaction in the same conditions as explained above.

On FIG. 20B, the molecule of formula (X) is reacted with an alkyne functionalized molecule of interest (XI) to give the molecule (XII) by a click chemistry reaction in the same conditions as explained above.

Another object of the invention is a method for the preparation of a molecule of formula (XV), or (XII), wherein said method comprises the step of reacting an alkyne function attached to R with an azide substituted phosphodiester derivative of the oligonucleotide as depicted on FIGS. 20A and 20B.

Molecules of formula (X), (XII), (XVI) and (XV) depicted hereunder are another object of the invention:

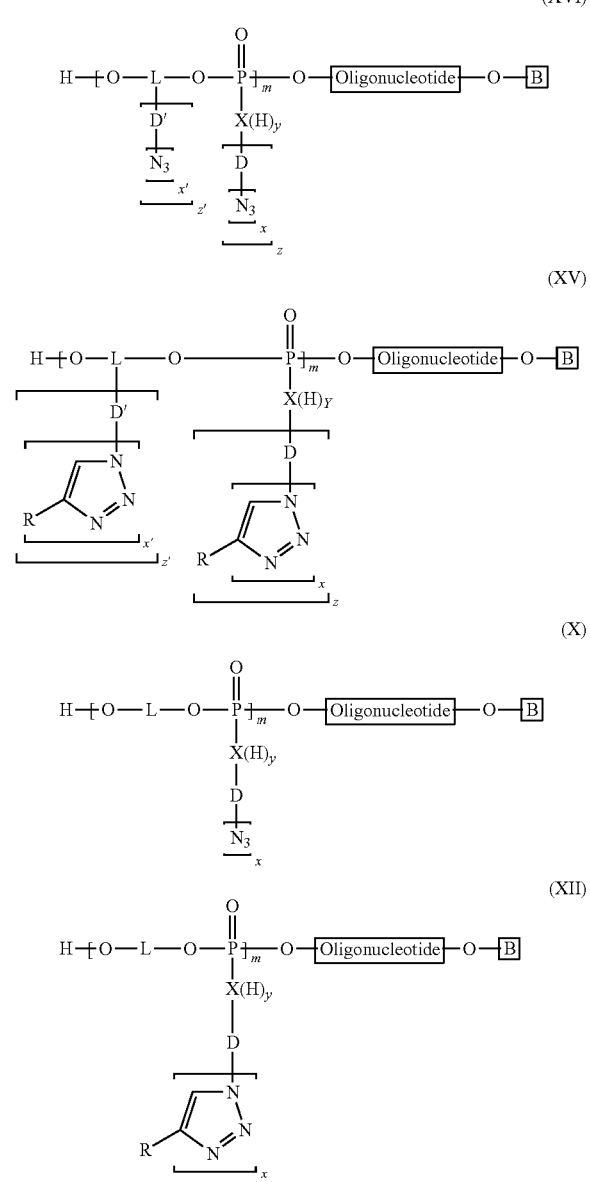

The variables L, X, D, B, R, m, x, y are identical to those of formula (I) and (III):

X is selected from N, O, S, an alcane di-yl comprising 1 to 12 carbon atoms, like —$CH_2$—, —$CH_2$—$CH_2$— ... ; preferentially X is selected from N, O;

m is an integer, $m \geq 1$

L is a linker which may be selected from the following list: alcane poly-yl functions with 1 to 12 carbon atoms, linear branched or cyclic possibly interrupted by one or several oxygen (—O—), nitrogen (—NH—, —N=) or sulphur (—S—) bridges or phosphodiester [—O—($O^-$)P(=O)—O—] bridges; in (X) and (XII), L is an alcane di-yl function with 1 to 12 carbon atoms, linear branched or cyclic possibly interrupted by one or several oxygen (—O—), nitrogen (—NH—, —N=) or sulphur (—S—) bridges or phosphodiester [—O—($O^-$)P(=O)—O—] bridges;

x is an integer, $30 \geq x \geq 1$ x' is an integer, $30 \geq x' \geq 1$

D is a linker between X and the azide group(s) (formula (X)) or one N atom of the triazole ring (formula (XII)). According to the value of x, D's valency is 2 or more. Preferably, D is selected from alcane poly-yl groups comprising 1 to 36 carbon atoms, possibly interrupted by one or several oxygen (—O—), nitrogen (—NH—, —N=) or sulphur (—S—) bridges or phosphodiester [—O—($O^-$)P(=O)—O—] bridges;

According to the choice of X and D, y is 0, 1 or 2;

D' is a linker between L and the azide group(s) (formula (XVI)) or one N atom of the triazole ring (formula (XV)). According to the value of x', D''s valency is 2 or more. Preferably, D' is selected from alcane poly-yl groups comprising 1 to 36 carbon atoms, possibly interrupted by one or several oxygen (—O—), nitrogen (—NH—, —N=) or sulphur (—S—) bridges or phosphodiester [—O—($O^-$)P(=O)—O—] bridges.

z and z' are integers, z and $z' \geq 0$, at least one of z and z' is $\geq 1$;

In formula (X), (XII), (XVI) and (XV) B is selected from H, a solid support (array, polymer, beads) or a tag.

On formula (X) and (XVI) of FIGS. 20A and 20B, the oligonucleotide is substituted by the phosphonate chain either on its 3'-extremity, on its 5'-extremity or inside of the sequence, one P atom being part of the oligonucleotide chain. According to a variant similar to that illustrated on FIG. 12, the oligonucleotide of formula (X) or (XIV) can be an oligonucleotide derivative wherein one or several phosphate function(s) of the oligonucleotide chain has been replaced by a phosphoramidate group of the type:

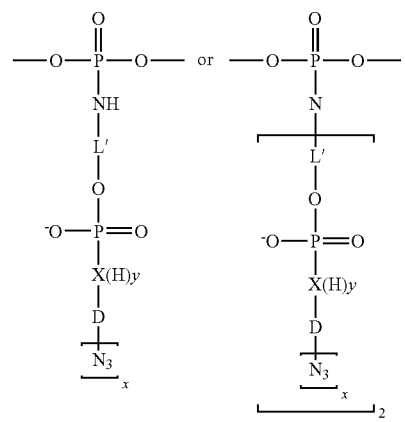

in which L' is an alcane di-yl chain comprising 1 to 12 carbon atoms.

In that case, the P atom at the extremity of the phosphodiester chain is not part of the oligonucleotide chain, but is linked to the oligonucleotide chain through a P—NH-L'—O—P link.

The grafted nucleotides of formula (X), (XII), (XIV), and formula (XV) can be in solution (case when B=H or a tag), or it can comprise a grafting to a solid support by one of its extremities (case when B=solid support).

The molecule of interest R is grafted by an alkyne function. When the alkyne-functionalized molecule of interest (XI) is contacted with the oligonucleotide derivative (XVI), or (X) in appropriate quantity, a 1,3-dipolar cycloaddition occurs leading to the triazole (XV), respectively (XII).

This 1,3-dipolar cycloaddition is very chemoselective, only occurring between alkynyl and azido functional groups with high yields. The resulting 1,2,3-triazoles are stable at high temperature and in aqueous conditions.

The molecule of interest can be any molecule for which there is an interest at obtaining a condensation product with an oligonucleotide. For the sake of illustration, mention may be made of: carbohydrates, peptides, lipids, oligonucleotides, biotin, ferrocenyl compounds, fluorescent tags . . . .

Figure 21:
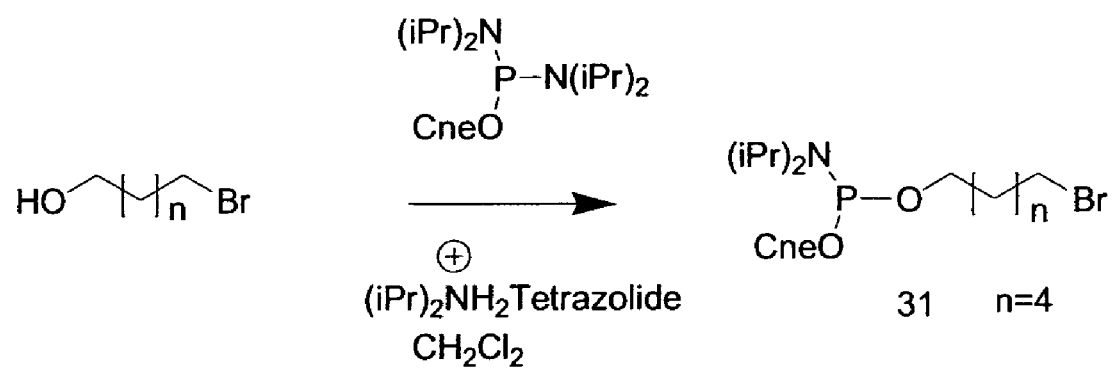

It is not possible to introduce directly an azide function on a phosphoramidite group, because the P atom reacts by a Staudinger reaction with the azide function. Consequently, another strategy illustrated on FIG. 21 has been designed to produce molecules (X) (XII), (XVI) and (XV), which consists in introducing a Br atom (or another leaving group) on the phosphoramidite group, elongating the nucleotide chain and then substituting the Br atom by an azido function.

Figure 22:
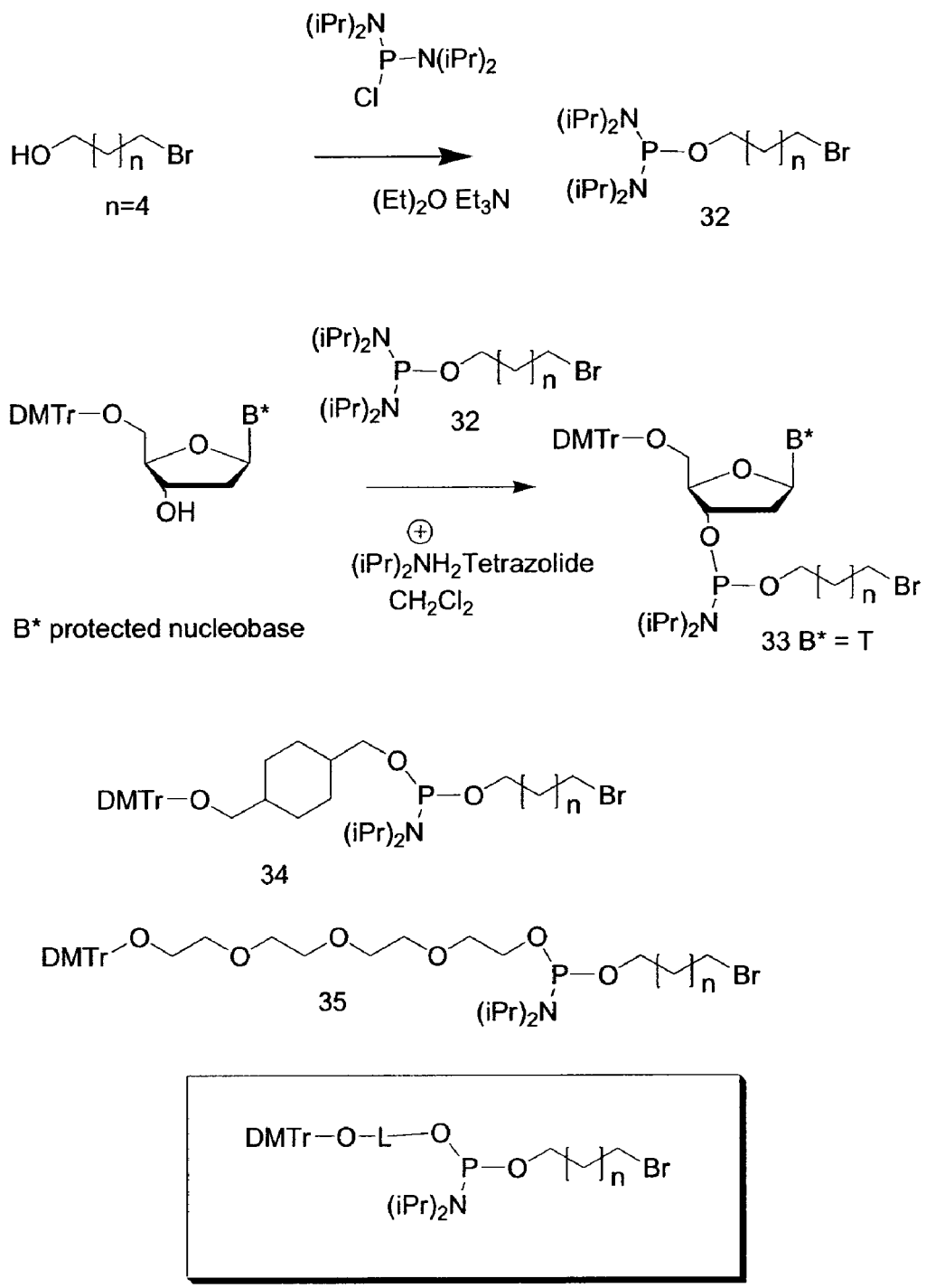

FIG. 22 illustrates several Br-substituted phosphoramidite derivatives and a method to graft them on a nucleotide.

Another object of the invention is a molecular array of formula (X), (XII), (XVI) or of formula (XV) consisting of a solid support grafted by a molecule as depicted above, respectively in formula (X) (XII), (XVI) or formula (XV) in a covalent or non covalent manner.

Solid supports like glass plaques, glass beads or silicone plaques, resins or polymers substituted by molecules that respond to formula (III), (XIII), (XII) or (XV) are another object of the invention. Especially when R is a carbohydrate or a carbohydrate derivative such molecular arrays are of interest for the study of interactions of carbohydrates with other molecules. Carbohydrates are of a high importance in biological processes and the study of their interactions with other molecules is of high importance for understanding biological mechanisms and for designing new potential drugs. There are few methods for preparing molecular arrays comprising carbohydrate grafting and not all of them are satisfying. Molecules of formula (III) (XIII), (XII) or (XV) with B=solid support in themselves constitute such molecular arrays.

According to another variant, a solid support of the invention can also be an oligonucleotide microarray, on which oligonucleotides are covalently immobilized into each microreactor. Different spots with different nucleotide sequences hybridise specifically with the complementary sequence carried by the molecule responding to formula (III), (XIII), (XII) or (XV), wherein B is H or a tag. H-bonds of the Watson-Crick type are built between the nucleotides attached to the micro-array and the molecule of formula (III), (XIII), (XII) or (XV).

The microarrays of the invention can be used to investigate interactions between the R group of the molecules of formula (III), (XIII), (XII) or (XV) and a target, especially a biological target. The invention is also directed to a method of investigation of interactions between the R group of the molecules of formula (III), (XIII), (XII) or (XV) and a target, especially a biological target, wherein said method comprises the step of contacting a solid support grafted by a molecule of formula (III), (XIII), (XII) or (XV) and the biological target The method of the invention gives access to carbohydrate arrays in a simple and efficient manner. Especially, starting from a DNA array, the reactions of phosphodiester synthesis followed by the introduction of an alkyne function on phosphorus and "click reaction" with an azido-grafted carbohydrate or carbohydrate derivative is a simple sequence of operation to obtain a carbohydrate array.

The molecules of formula (III), (XIII), (XII) or (XV) can also be used for the vectorisation of an oligonucleotide to a biological target. Molecules of interest, like carbohydrates, can be selected for their specificity for a certain type of cells, so that they will help transporting the nucleotide to which they are bound to its intended target. More specifically, the invention is concerned by a method for the vectorisation of an oligonucleotide to a biological target in a subject to be treated, wherein a carbohydrate is selected for its specificity for a certain type of cells comprised in the biological target, and said carbohydrate is attached to the oligonucleotide by the method of the invention and the resultant molecule (III), (XIII), (XII) or (XV) is administered to the subject to be treated.

Experimental Part

Introduction

A versatile approach has been developed for the multiple labeling of oligonucleotides. First, three linkers as a H-phosphonate monoester derivative were condensed on a solid-supported $T_{12}$ to introduce H-phosphonate diester linkages which were oxidized in presence of propargyl amine. Secondly, three galactosyl azide derivatives were conjugated to the solid-supported three alkynes-modified $T_{12}$ by a 1,3-cycloaddition so called "click chemistry" in presence of Cu(I) assisted by microwaves, as illustrated on FIG. 8.

Figure 9:
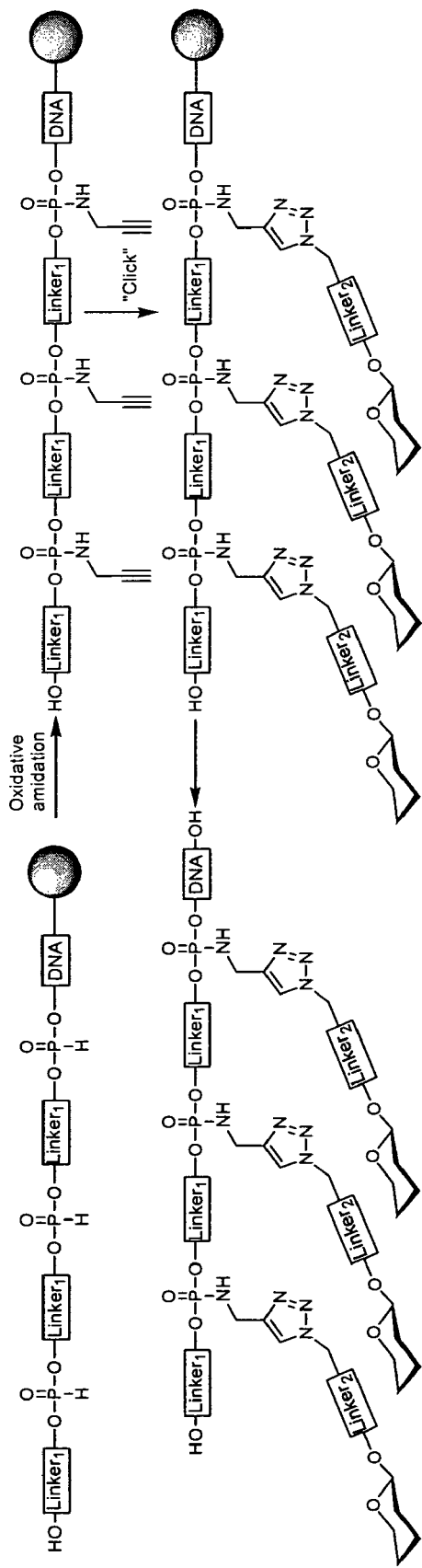

According to the invention a general, simple, robust and versatile strategy for anchoring one or several carbohydrate derivative(s) to a solid-supported oligonucleotide has been conceived and performed (FIG. 9). The 1,3-dipolar cycloaddition between alkynes and azides, so-called "click" chemistry (Kolb, H. C.; Finn, M. G.; Sharpless, K. B. *Angew. Chem., Int. Ed.* 2001, 40, 2004-2021; Bock, V. D.; Hiemstra, H.; van Maarseveen, J. H. *Eur. J. Org. Chem.* 2006, 51-68) was applied to attach carbohydrate residues to the oligonucleotide backbone. Microwave activation significantly improved the reaction kinetic compared to standard conditions. Solid-supported reactions provided better results in terms of purity when compared to similar solution phase conditions where some phosphoramidate hydrolysis was observed.

The Huisgen's 1,3-dipolar cycloaddition between alkyne and azide is very attractive since it is nearly quantitative, can be performed in water with an organic co-solvent and multiple cycloadditions can be performed on multivalent scaffolds (Wang, Q.; Chan, T. R.; Hilgraf, R.; Fokin, V. V.; Sharpless, K. B.; Finn, M. G. *J. Am. Chem. Soc.* 2003, 125, 3192-3193) Furthermore, this reaction is orthogonal to most typical organic transformations and therefore highly chemoselective.

Experimental

1—Synthesis of solid-supported $T_{12}$ (2): The Solid-supported $T_{12}$ was synthesized using a DNA synthesizer (ABI 381A) using standard phosphoramidite chemistry on a commercially available thymidine succinyle CPG solid support (500A). Then 1 (15 molar eq., 60 mM in $C_5H_5N/CH_3CN$, 1:1, v/v) was coupled using a H-phosphonate chemistry cycle with pivaloyl chloride as activator (200 mM in $C_5H_5N/CH_3CN$, 1:1, v/v) and 3% dichloroacetic acid in $CH_2Cl_2$ for the detritylation step.

2—General procedure for amidative oxidation: The solid-supported oligonucleotide (1 µmol) was treated, back and forth using two syringes, with a solution of 10% propargylamine (100 µL) in $CCl_4/C_5H_5N$ (900 µL, 1:1, v/v) for 30 min. The CPG beads were washed with $C_5H_5N$ (1 mL) and MeCN (3×2 mL), and then dried by flushing with nitrogen.

3—General procedure for Cu(I)-catalyzed 1,3-dipolar cycloaddition: To a solid-supported oligonucleotide (0.5 µmol) were added protected galactosyl azide 4 (10 eq, 5 µmol, 100 µL of a 50 mM solution in MeOH), $CuSO_4$ (0.4 eq, 0.2 µmol, 5 µL of a 40 mM solution in $H_2O$), freshly prepared sodium ascorbate (2 eq, 1 µmol, 20 µL of a 50 mM solution in H₂O) and water (75 μL). The resulting preparation in a sealed tube was treated with a microwave synthesizer Initiator™ from Biotage set at 100 W with a 30 sec pre-mixing time. The solution was removed and the CPG beads were washed with H₂O/MeOH (2 mL, 1:1, v/v) and MeOH (1 mL) then dried.

4—General procedure for deprotection: The beads were placed into a sealed vial and treated with concentrated aqueous ammonia (1 mL) for 4 h at room temperature. The beads were filtered off and the solution was evaporated. The residue was dissolved in water for subsequent analyses.

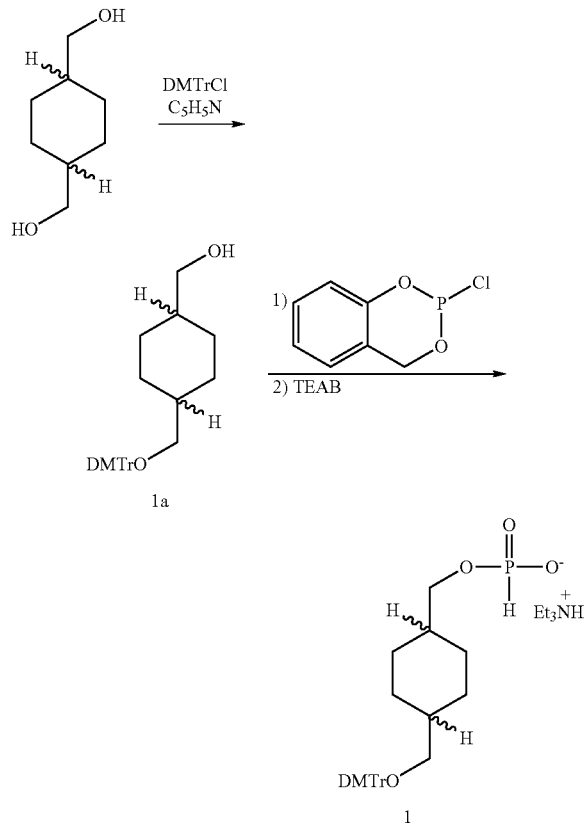

[4-(Dimethoxytrityloxymethyl)cyclohexyl]methanol 1a 1,4-cyclohexanedimethanol (mixture of cis and trans) (2.88 g, 20 mmol) was co-evaporated with anhydrous pyridine (2×25 mL) then taken up in pyridine (25 mL). 4,4'-dimethoxytrityl chloride (5.08 g, 15 mmol) was added in three portions over 30 minutes and the mixture was stirred at r.t. for 3 h. The solvent was evaporated and the syrupy residue was dissolved in EtOAc (200 mL). The organic layer was washed with saturated aqueous NaHCO₃ (2×50 mL) and brine (2×50 mL), dried (Na₂SO₄), and evaporated. The residue was purified by flash silica gel column chromatography (0 to 5% MeOH in CH₂Cl₂ containing 0.5% of Et₃N) to afford 1a (4.02 g, 45%) as a pale yellow oil.

$R_f$=0.70 (CH₂Cl₂/MeOH, 95:5, v/v).

¹H NMR (CDCl₃, 400 MHz): δ 1.02-1.93 (4 m, 11H), 2.94-3.03 (m, 2H), 3.47-3.51 (m, 2H), 3.85 (s, 6H), 6.85-7.50 (m, 13H).

¹³C NMR (CDCl₃, 100 MHz): δ 25.5, 26.0, 29.1, 29.7, 36.2, 38.1, 38.8, 40.7, 55.2, 66.0, 66.2, 68.6, 68.7, 113.0, 113.2, 126.6, 127.7, 127.8, 129.2, 130.1, 136.1, 136.8, 145.5, 158.4, 158.7.

HRFAB (positive mode, nitrobenzyl alcohol) m/z: calcd for C₂₉H₃₄O₄ [M]⁺ 446.2457. found 446.2435.

Triethylammonium [4-(dimethoxytrityloxymethyl)cyclohexyl]methyl Hydrogen Phosphonate 1

1a (893 mg, 2 mmol) was co-evaporated with anhydrous pyridine (2×10 mL) then taken up in pyridine (10 mL) and CH₂Cl₂ (10 mL). 2-chloro-1,3,2-phosphorin-4-one (Marugg, J. E.; Tromp, M.; Kuyl-Yeheskiely, E.; van der Marel, G. A.; van Boom, J. H. *Tetrahedron Lett*. 1986, 27, 2661-2664) (506 mg, 2.5 mmol) was added and the mixture was stirred for 2 h. 1M TEAB (20 mL) was added and the solution was stirred until the formation of CO₂ bubbles stopped. The organic layer was separated and the aqueous layer was extracted with CH₂Cl₂ (2×20 mL). The organic layers were combined, dried (Na₂SO₄) and evaporated. The residue was purified by flash silica gel column chromatography (0 to 5% MeOH in CH₂Cl₂ containing 1% of Et₃N) to afford 1 (550 mg, 45%) as a colorless oil.

$R_f$=0.15 (CH₂Cl₂/MeOH/Et₃N 89:3:8, v/v/v).

¹H NMR (CDCl₃, 400 MHz): δ 0.82-1.73 (m, 19H), 2.94 (m, 6H), 2.75-2.84 (m, 2H), 3.51-3.58 (m, 2H), 3.63, 3.65 (2s, 6H), 6.68-7.34 (m, 13H).

¹³C NMR (CDCl₃, 100 MHz): δ 8.5, 25.7, 25.9, 29.2, 29.6, 36.0, 36.4, 38.6, 38.9, 45.3, 55.1, 55.2, 66.4, 66.6, 68.6, 69.2, 112.9, 113.1, 126.5, 127.0, 127.6, 127.78, 127.83, 128.2, 129.2, 130.0, 130.1, 136.67, 136.70, 145.4, 158.3, 158.6.

³¹P NMR (CD₃CN, 80 MHz): δ 7.32, 7.60 (2s, P).

HRFAB (negative mode, nitrobenzyl alcohol) m/z: calcd for C₂₉H₃₄O₆P₁ [M-Et₃NH]⁻ 509.2096. found 509.2092.

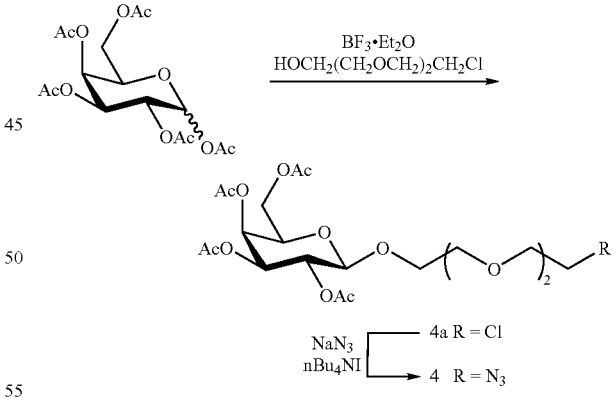

1-Chloro-3,6-dioxaoct-8-yl 2,3,4,6-tetra-O-acetyl-β-D-galactopyranoside 4a

A solution of 2-[2-(2-chloroethoxy)ethoxy]ethanol (2.80 mL, 19.2 mmol) and the peracetylated D-galactose (5 g, 12.8 mmol) in anhydrous CH₂Cl₂ (50 mL) was cooled at 0° C. before dropwise addition of BF₃.Et₂O (8.12 mL, 64.0 mmol). The reaction mixture was stirred at r.t. for 24 hrs then poured into saturated aqueous NaHCO₃ (300 mL). The aqueous layer was extracted with CH₂Cl₂ (2×200 mL). The organic layers were combined, dried (Na$_2$SO$_4$), filtered and evaporated under reduced pressure. The oily residue was purified by flash silica gel column chromatography (PE then PE/EtOAc 3:2) to afford 4a (Wang, J.; Zhang, B.; Fang, J.; Sujino, K.; Li, H.; Otter, A.; Hindsgaul, O.; Palcic, M. M.; Wang, P. G. *J. Carbohydr. Chem.* 2003, 22, 347-376) (2.93 g, 61%) as a pale yellow oil.

$^1$H NMR (CDCl$_3$, 300 MHz): δ 1.99, 2.05, 2.07, 2.15 (4s, 4×3H), 3.60-3.70 (m, 8H), 3.71-3.82 (m, 3H), 3.84-4.02 (m, 2H), 4.06-4.22 (m, 2H), 4.58 (d, 1H, J$_{1,2}$=8.0 Hz), 5.02 (dd, 1H, J$_{3,4}$=3.4 Hz, J$_{3,2}$=10.4 Hz), 5.22 (dd, 1H, J$_{2,1}$=8.0 Hz, J$_{2,3}$=10.4 Hz), 5.39 (dd, 1H, J$_{4,5}$=0.9 Hz, J$_{4,3}$=3.4 Hz). $^{13}$C NMR (CDCl$_3$, 75 MHz): δ 20.6, 20.7, 20.8, 21.0, 42.7, 61.2, 67.0, 68.7, 69.0, 70.3, 70.58, 70.61, 70.63, 70.8, 71.3, 101.3, 169.4, 170.1, 170.2, 170.4.

1-Azido-3,6-dioxaoct-8-yl 2,3,4,6-tetra-O-acetyl-β-D-galactopyranoside 4

A solution of 4a (3.85 g, 7.71 mmol), sodium azide (2.51 g, 38.58 mmol) and nBu$_4$NI (5.7 g, 15.43 mmol) in anhydrous DMF (20 mL) was stirred at 90° C. for 24 hrs. The solution was cooled to r.t. then diluted with EtOAc (300 mL). The organic layer was washed with water (3×200 mL), dried (Na$_2$SO$_4$), filtered and evaporated under reduced pressure. The oily residue was purified by flash silica gel column chromatography (PE then PE/EtOAc 1:1) to afford 4 (3.29 g, 85%) as a pale yellow oil.

$^1$H NMR (CDCl$_3$, 300 MHz): δ 1.99, 2.04, 2.07, 2.15 (4s, 4×3H), 3.40 (t, 2H, J=5.0 Hz), 3.60-3.82 (m, 9H), 3.88-4.02 (m, 2H), 4.08-4.20 (m, 1H), 4.59 (d, 1H, J$_{1,2}$=7.9 Hz), 5.02 (dd, 1H, J$_{3,4}$=3.4 Hz, J$_{3,2}$=10.5 Hz), 5.21 (dd, 1H, J$_{2,1}$=7.9 Hz, J$_{2,3}$=10.5 Hz), 5.39 (dd, 1H, J$_{4,5}$=0.7 Hz, J$_{4,3}$=3.4 Hz).
$^{13}$C NMR (CDCl$_3$, 75 MHz): δ 20.3, 20.4, 20.5, 20.8, 50.4, 61.1, 66.8, 68.6, 68.8, 69.8, 70.1, 70.4, 70.4, 70.5, 70.7, 101.1, 169.2, 169.9, 170.0, 170.1.

HRFAB (positive mode, thioglycerol) m/z: calcd for C$_{20}$H$_{32}$N$_3$O$_{12}$ [M+H]+506.1986. found 506.1968. [α]$_D$=+1.4 (c=1, CH$_2$Cl$_2$).

Trigalactosylated T$_{12}$* 6:

We first prepared a cyanoethyl-protected dodecathymidine (T$_{12}$*) on solid support using well established phosphoramidite chemistry (Beaucage, S. L.; Caruthers, M. H. *Tetrahedron Lett.* 1981, 22, 1859-1862). Then three H-phosphonate diester linkages were introduced using H-phosphonate monoester 1 to yield the modified supported oligonucleotide 2 (FIG. 8). An amidative oxidation with CCl$_4$ in the presence of propargylamine afforded the alkyne-functionalized oligonucleotide 3 with three propargyl phosphoramidate linkages. An aliquot was treated with aqueous ammonia and analyzed by HPLC/MS to determine the efficiency of these synthetic steps (i.e. three H-phosphonate couplings and amidative oxidation). The first H-phosphonate coupling was not complete (86-94%) while the two subsequent couplings were higher yielding. The resulting mixture was composed of 3 (~75%), unreacted T$_{12}$ (~14%) and intermediates with one (~3%) and two propargyl groups (~4%) as determined by MALDI-TOF MS analyses.

Oligonucleotide 3 was then used to optimize the 1,3-dipolar cycloaddition with azide derivative 4. The reaction proceeds slowly at room temperature and was therefore performed under microwave (MW) to shorten reaction times. Several reaction conditions under microwave activation were investigated with temperatures ranging from 60 to 100° C. and reaction times from 60 to 15 min (Table 1). The cycloaddition was performed between the trivalent alkyne oligonucleotide 3 and the monovalent azide 4 with 3.3 molar eq of azide per alkyne residue in the presence of CuSO$_4$/sodium ascorbate (Rostovtsev, V. V.; Green, L. G.; Fokin, V. V.; Sharpless, K. B. *Angew. Chem., Int. Ed.* 2002, 41, 2596-2599) in water/methanol to yield the solid-supported protected trigalactosylated oligonucleotide 5. Subsequent treatment of 5 with aqueous ammonia afforded the fully deprotected trigalactosylated T$_{12}$ 6 in solution. The percentage of cycloaddition was determined by HPLC/MS analysis of the crude material (FIG. 10). The main peak (R$_T$~20 min) corresponds to the expected trigalactosylated T$_{12}$ 6, the broad peak at ~18 min corresponds to the digalactosylated T$_{12}$ formed from the dialkyne T$_{12}$, the two peaks at ~16 min correspond to the monogalactosylated T$_{12}$ formed from the monoalkyne T$_{12}$ and the peak at ~15 min is the T$_{12}$. The splitting of HPLC peak is due to the presence of diastereoisomers since the phosphorous atom of the phosphoramidate linkage is chiral. The pure trigalactosylated T$_{12}$ 6 was easily isolated by HPLC and characterized by MALDI-TOF MS.

The results of cycloaddition are summarized in Table 1. Impurities with one and two alkynes leading to the mono- and bis-cycloadducts were not considered but proceeded with the same efficiency. It is worth pointing out that cycloaddition on the cyanoethyl protecting groups was not observed under these conditions.

TABLE 1

Microwave assisted 1,3-dipolar cycloaddition on solid-support of alkyne-functionalized oligonucleotide 3 (0.5 μmol) and galactosyl azide derivative 4 (5 μmol, 3.3 molar eq./alkyne) with CuSO$_4$ (0.2 μmol) and sodium ascorbate (1 μmol) in MeOH/H$_2$O (200 μL, 1:1, v/v) under MW activation (100 W).

| Entry | Temperature (° C.) | Time(min) | Conversion[a] % |
|---|---|---|---|
| 1 | 100 | 20 | 100 |
| 2 | 75 | 20 | 100 |
| 3 | 60 | 20 | 100 |
| 4 | 60 | 15 | 84[b] |
| 5 | 20[c] | 420 | 73 |

[a] conversion to the triply functionalized oligonucleotide 3.
[b] contaminated with one unreacted alkyne residue.
[c] without microwave activation.

The first attempt was performed at 100° C. with 20 min MW activation (entry 1) and complete conversion of all three alkyne residues into the desired triazoles was observed. Decreasing the temperature to 75 then 60° C. also gave a complete reaction within 20 min (entries 2 and 3). Nevertheless, conversion was not complete when the temperature was kept at 60° C. and time reduced to 15 min where 16% of digalactosylated T$_{12}$ with one remaining alkyne residue was detected by HPLC/MS (entry 4). Finally, the reaction did not reach completion (73%) even after 7 h without MW activation (entry 5).

Similarly, the cycloaddition reaction was performed in solution on the T$_{12}$ phosphodiester with three alkyne phosphoramidate linkages and was complete either within 20 min at 75° C. under MW or 18 h without MW. Nevertheless, hydrolysis of one phosphoramidate P—N bond was observed affording the corresponding phosphodiester (13% under MW and 20% without MW). No decomposition of the solid-supported oligonucleotide 5 was observed when the reaction was performed even at 100° C. for 60 min under MW activation.

In conclusion, we observed a very efficient click coupling of alkyne-bearing oligonucleotide 3 with azide-functionalized galactoside 4 under MW activation at 60° C. for 20 min. The reaction could be performed on solid support or in solution under similar conditions. The main advantages of the solid-supported microwave assisted click chemistry are: 1) introduction of several alkynes anywhere within the oligonucleotide backbone (i.e. at the 3'- or 5'-end or in the oligonucleotidic sequence) (Laurent, A.; Naval, M.; Debart, F.; Vasseur, J. J.; Rayner, B. *Nucleic Acids Res.* 1999, 27, 4151-4159); 2) modulation of the distance between each alkyne using different diol-type linkers between each H-phosphonate diester function; 3) cycloadditions can be performed with an oligonucleotide on solid support or in solution; 4) use and recovery of excess azide derivatives; 5) conjugation of various azides to an oligonucleotide using this approach; 6) rapid and high yielding multiple 1,3-dipolar cycloadditions and lack of hydrolysis of the phosphoramidate bonds.

Variant:

A variant was performed with the following dialkyne phosphoramidite which can be grafted on an oligosaccharide once or twice.

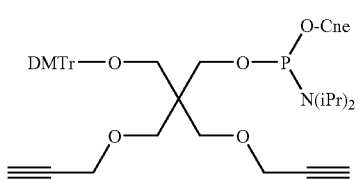

Figure 11:
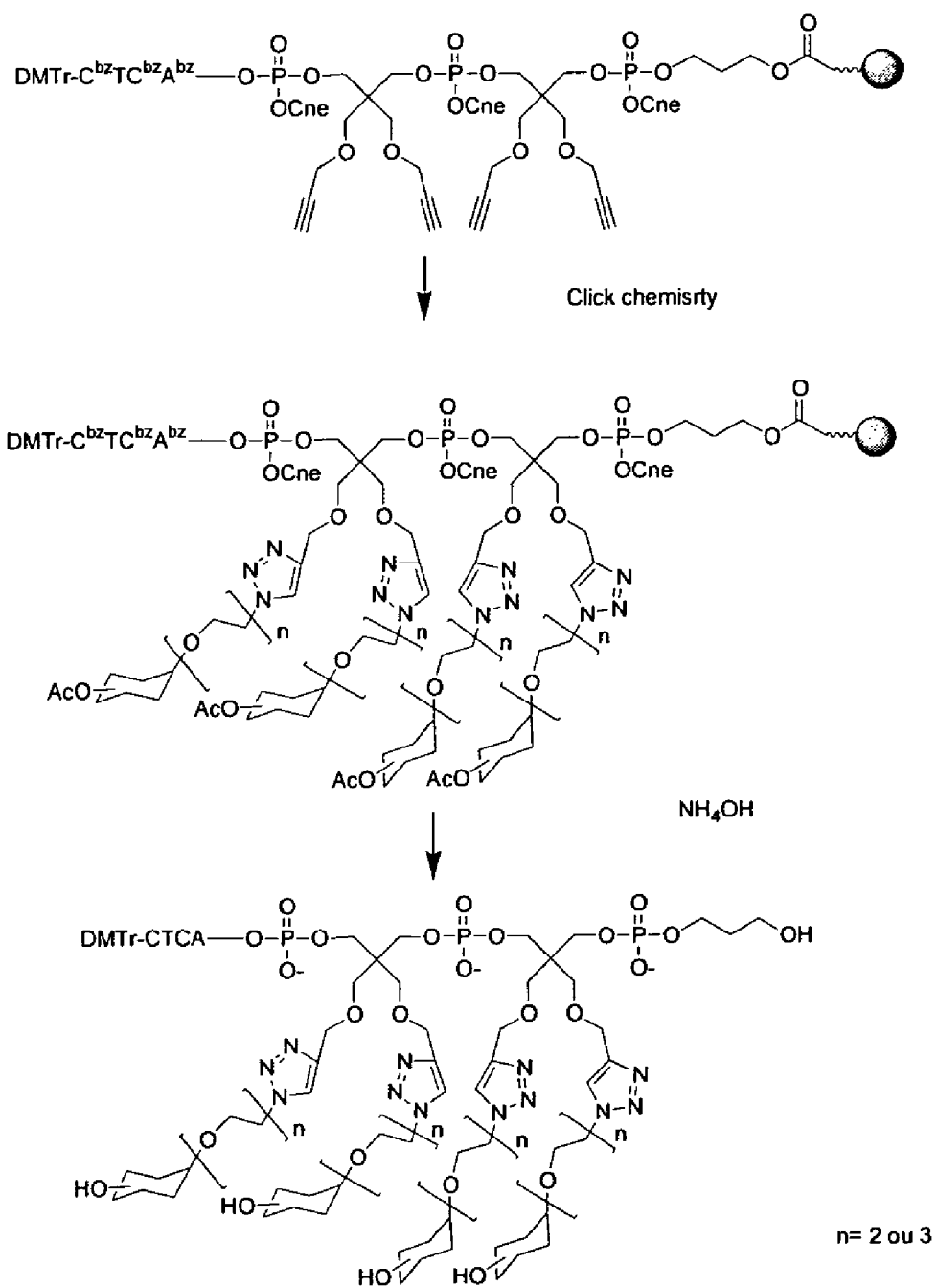

A tetramer was synthesized (FIG. 11) and conjugated through click chemistry with an azide sugar.

Then the oligonucleotide can be lengthened and marked with CY3.

Preparation of a Molecular Array:

According to the invention, DNA chips (DNA display) are used as an addressing tool for mixed DNA/Oligosaccharide molecules. We implement microreactors by etching soda-lime glass. The surfaces are functionalized and activated leading to NHS ester activated surfaces. Each type of oligonucleotide is covalently immobilized into each microreactor. Different spots with different nucleotide sequences will hybridise specifically with the complementary sequence carried by the oligosaccharide.

As illustrated in the examples above, chimeric molecules bearing an oligosaccharide moiety and an oligonucleotide have been synthesized with different valences of saccharides and different spacers. They were analysed by HPLC and characterized by MALDI-ToF.

Results: Chimeric molecules bearing up to three galactose molecules were synthesized with spacers comprising two or three TEG units or 1,4-dimethylcyclohexane. 600 microreactors of 700 μm diameter and 100 μm deep with an average roughness of 3 nm were fabricated on glass slide.

Oligonucleotides were immobilised via an amide bond and the chimeric molecules were locally addressed through hybridization on the solid support. Lectin recognition assays were performed and followed by scanning fluorescence.

Preparation of Poly Alkyne Functionalized Phosphoester or Phosphoramidate Derivatives

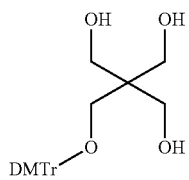

O-(4,4'-dimethoxytrityl)-pentaerythritol (7). Pentaerytritol (2.7 g, 20 mmol) was dried by co-evaporation in dry pyridine (3×10 mL) and then dissolved in dry pyridine (120 mL). Dimethoxytrityl chloride (5.42 g, 16 mmol) was added to the solution and the reaction was stirred at room temperature for 16 h. The reaction was quenched with methanol (2 mL), stirred for 10 min then poured into aqueous saturated $NaHCO_3$ (300 mL). The aqueous layer was extracted with $CH_2Cl_2$ (3×150 mL). The organic layers were combined, dried ($Na_2SO_4$), filtered and evaporated. The residue was purified by chromatography on silica gel ($CH_2Cl_2$/MeOH 99:1 to 94:6, v/v) affording the mono-dimethoxytritylated pentaerythritol 7 (2.2 g, 30%) as pale yellow foam. $R_f$=0.50 ($CH_2Cl_2$/MeOH, 9:1, v/v). $^1H$ NMR ($CDCl_3$, 400 MHz): δ 2.36 (br s, 3H), 3.10 (s, 2H), 3.65 (br s, 6H), 3.71 (s, 6H), 6.74-7.31 (m, 13H). $^{13}C$ NMR ($CDCl_3$, 100 MHz): δ 45.3, 53.5, 55.2, 63.9, 64.6, 86.5, 113.3, 127.0, 128.0, 130.0, 135.6, 144.6, 158.6.

Décrit dans Kim, S. J.; Bang, E.-K.; Kim, B. H. *Synlett* 2003, 1838-1840.

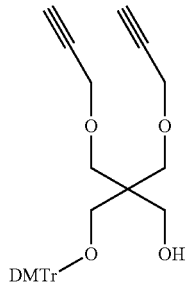

1-O-(4,4'-dimethoxytrityl)-2,2-bis-propargyloxymethyl-1,3-propanediol (8). Sodium hydride (1.16 g, 29.1 mmol, 60% in oil) was added at 0° C. to a solution of mono-dimethoxytritylated pentaerythritol 7 (2.2 g, 4.8 mmol) in dry THF (30 mL). The reaction was stirred for 10 min before adding propargyl bromide (3.3 mL, 29.1 mmol, 80% in toluene) at rt. The resulting milky solution was stirred for an additional 3 h at rt. The solution was diluted with $CH_2Cl_2$ (80 mL) and the organic layer was washed with cold water (50 mL), brine (50 mL), dried ($Na_2SO_4$), filtered and evaporated. The residue was purified by chromatography on silica gel ($CH_2Cl_2$/MeOH 99.5:0.5 to 97:3, v/v) affording the dimethoxytritylated bis-propargylated pentaerythritol 2 (2.2 g, 89%) as pale yellow foam. $R_f$=0.45 (cyclohexane/$CH_2Cl_2$/$Et_3N$, 7:2:1, v/v/v). $^1H$ NMR ($CDCl_3$, 400 MHz): δ 2.35 (m, 3H), 3.05 (s, 2H), 3.48-3.60 (m, 6H), 3.70 (s, 6H), 4.02 (s, 4H), 6.73-7.26 (m, 13H). $^{13}C$ NMR ($CDCl_3$, 100 MHz): δ 11.7, 45.1, 46.3, 53.5, 55.2, 58.7, 62.3, 65.3, 70.3, 74.5, 86.0, 113.0, 113.1, 126.7, 127.8, 128.2, 129.2, 130.1, 136.0, 145.0, 158.4. HRFABMS (positive mode, nitrobenzylic alcohol) m/z: calcd for $C_{32}H_{34}O_6$ $[M+H]^+$ 514.2355. found 514.2365

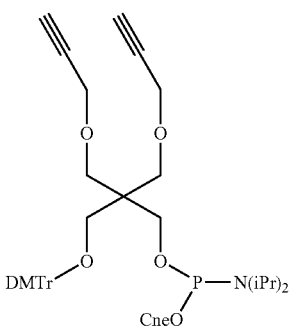

1-O-(4,4'-dimethoxytrityloxymethyl)-2,2-bis-propargyloxymethyl-3-{O-[(2-cyanoethyl)-N,N-diisopropyl-phosphoramidite]-1,3-propanediol (9). 1-O-(4,4'-dimethoxytrityl)-2,2-bis-propargyloxymethyl-1,3-propanediol 8 (680 mg, 1.32 mmol) and diisopropylammonium tetrazolide (113 mg, 0.66 mmol) were dried three times by co-evaporation with anhydrous acetonitrile then dissolved in anhydrous $CH_2Cl_2$ (8 mL) before addition of 2-cyanoethyl tetraisopropylphosphorodiamidite (503 μL, 1.58 mmol) at rt. The resulting mixture was stirred at room temperature for 3 h then diluted with EtOAc (50 mL). The organic layer was washed with brine (2×100 mL), dried ($Na_2SO_4$), filtered and evaporated. The residue was purified by chromatography on silica gel (Cyclohexane/$CH_2Cl_2$ 100/0 to 80/20 with 4% $Et_3N$) affording the phosphoramidite 9 (800 mg, 85%) as an oil. $R_f$=0.60 (Cyclohexane/$CH_2Cl_2$/$Et_3N$, 7:2:1, v/v/v). $^1H$ NMR ($CDCl_3$, 200 MHz): δ 1.15-1.24 (m, 12H), 2.40 (m, 2H), 2.54 (t, 2H, J=6.5 Hz), 3.15 (br s, 2H), 3.45-3.74 (m, 10H), 3.81 (s, 6H), 4.09-4.12 (m, 4H), 6.76-7.49 (m, 13H). $^{13}C$ NMR ($CDCl_3$, 100 MHz): δ 20.3, 20.4, 24.6, 24.6, 26.92, 26.93, 29.7, 30.2, 30.3, 43.0, 43.1, 43.5, 45.5, 45.6, 46.3, 53.4, 55.2, 58.2, 58.4, 58.6, 58.7, 61.2, 62.2, 62.4, 69.4, 74.1, 74.2, 80.0, 85.6, 112.9, 117.7, 126.6, 127.6, 128.3, 130.3, 136.3, 145.3, 158.3. $^{31}P$ NMR ($CDCN_3$, 80 MHz): δ 148.6. HRFABMS (positive mode, nitrobenzylic alcohol) m/z: calcd for $C_{41}H_{52}O_7N_2P_1$ $[M+H]^+$ 715.3512. found 715.3522.

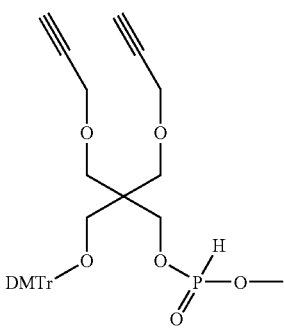

1-O-(4,4'-dimethoxytrityloxymethyl)-2,2-bis-propargyloxymethyl-3-O—(H-phosphonate monoester triethylammonium)-1,3-propanediol (10)

1-O-(4,4'-dimethoxytrityl)-2,2-bis-propargyloxymethyl-1,3-propanediol (8) (514 mg 1 mmol) was dried by co-evaporation in dry pyridine (3×5 mL) and then dissolved in dry pyridine (6 mL). Diphenylphosphite (1.4 mL 7 mmol) was added and the solution was stirred at RT for 60 min. Then the mixture was cold down (5° C.) and a solution of water and triethylamine (5 mL, 1:1, v/v) was added. The resulting solution was stirred for 45 min at RT. The product was poured in a separatory funnel containing aqueous saturated $NaHCO_3$, and extracted with CH2Cl2 (3×50 mL). Organic layer was dried over anhydrous $Na_2SO_4$, and evaporated to dryness under reduced pressure. The residue was purified by flash chromatography on silica gel using an increasing amount of methanol (0 to 7%) in $CH_2Cl_2$ containing 4% of $Et_3N$.

530 mg, 78%

Rf: 0.30 $CH_2Cl_2$, MeOH, $Et_3N$, (92.5:5:2.5, v/v/v), $^1H$ NMR (CD3CN, 400 MHz): δ 1.22 (t, 7.3 Hz 9H, CH3-CH2), 2.73 (s, 3H, HC), 2.97 (q 7.3 Hz, 6H, CH3-CH2), 3.04 (s, 2H, CH2ODMTr), 3.55 (s, 4H, CH2-Opropargyl), 3.73 (d, 6.2 Hz, 2H CH2OP), 3.79 (s, 6H, OCH3), 4.10 (d, 2.4 Hz, 4H, OCH2C), 6.56 (d, JHP=598 Hz, 1H, HP), 6.87-7.48 (m, 13H arom)

$^{13}C$ NMR (CD3CN, 100 MHz): δ 7.95, 45.3, 54.9, 58.3, 61.4, 62.3, 69.1, 74.8, 80.0, 85.5, 112.9, 126.7, 127.8, 128.1, 130.1, 136.2, 145.5, 158.6.

$^{31}P$ NMR ($CDCN_3$, 80 MHz): δ 7.1.

HRFABMS (negative mode, nitrobenzylic alcohol) m/z: calcd for $C_{32}H_{34}O_8P_1$ $[M-H]^-$, 577.1991 found 577.1975.

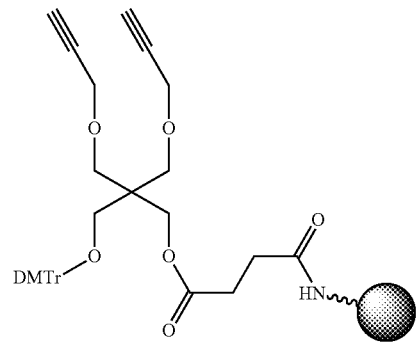

1-O-(4,4'-dimethoxytrityloxymethyl)-2,2-bis-propargyloxymethyl-3-O-(succinic-LCAA CPG)-1,3-propanediol (11)

(LCAA-CPG 500 Å, 80-120 mesh, 80-90 μmol/g)

LCAA-CPG (1.00 g), 1-O-(4,4'-dimethoxytrityl)-2,2-bis-propargyloxymethyl-1,3-propanediol 8 (0.114 g, 0.2 mmol), EDC (0.191 g, 1 mmol), DMAP (0.012 g, 0.1 mmol), $Et_3N$ (0.1 ml) were shaken in anhydrous pyridine (5 ml) at room temperature for 48 hours. Then pentachlorophenol (135 mg, 0.5 mmol) was added and the mixture was shaken for 10 h. Piperidine (5 mL) was added and after 5 min of shaking the solid support was filtered off, washed with $CH_2Cl_2$ and dried. A capping step with standard Cap A and Cap B solutions was applied for 2 hour and the solid support was filtered off, washed with $CH_2Cl_2$ and dried. Trityl assay indicated a loading of 40 μmol/g.

Serie 1,1,1-Tris(hydroxymethyl)ethane

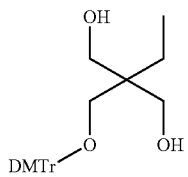

1-O-(4,4'-dimethoxytrityl)-2-hydroxymethyl-2-methyl-1,3-propanediol (16)

Same protocol than for 7.
1.9 g, 56%
$R_f$=0.28 ($CH_2Cl_2$/MeOH, 19:1, v/v).
$^1$H NMR ($CDCl_3$, 400 MHz): δ 0.87 (s, 3H, $CH_3$), 2.42 (br s, 2H, OH), 3.16 (s, 2H, DMTrO-$CH_2$—), 3.69 (d, 2H, $AB_{syst}$J=25.2 Hz —$CH_{2a}$OH) 3.64 (d, 2H, $AB_{syst}$J=25.2 Hz —$CH_{2b}$OH), 3.82 (s, 6H, $OCH_3$), 6.79-7.49 (m, 13H, arom.).
$^{13}$C NMR ($CDCl_3$, 100 MHz): 17.4, 41.1, 55.2, 67.2, 68.2, 86.3, 113.3, 126.9, 128.0, 130.0, 135.8, 144.7, 158.5.
HRFABMS (positive mode, nitrobenzylic alcohol) m/z: calcd for $C_{26}H_{30}O_5$ [M+H]$^+$ 422.2093. found 422.2098.

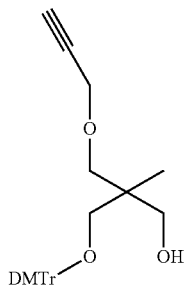

1-O-(4,4'-dimethoxytrityl)-2-propargyloxymethyl-2-methyl-1,3-propanediol (17)

1-O-(4,4'-dimethoxytrityl)-2-hydroxymethyl-2-methyl-1,3-propanediol 16 (620 mg, 1.47 mmol) was dissolved in anhydrous THF (6 mL) and sodium hydride (60% in oil, 590 mg, 14.7 mmol) was added. After 10 min stirring, propargyl bromide (80% in toluene, 650 mL, 5.9 mmol) was added and the mixture was stirred at RT for 1 h. Then $CH_2Cl_2$ was added (100 mL) and 2 mL of water. Organic layer was washed with water (2×100 mL) and dried over $Na_2SO_4$. After evaporation the residue was purified by flash chromatography using an increasing amount of ethyl acetate (10% to 50%) in cyclohexane containing 1% of triethylamine.
500 mg 74%
$^1$H NMR ($CDCl_3$, 200 MHz): δ 0.95 (s, 3H, $CH_3$), 2.58 (t, 1H, CCH), 2.60 (br s, 1H, OH), 3.03 (d, $AB_{syst}$J=20.7 Hz, 1H, $CH_{2a}$O-propargyl) 3.13 (d, $AB_{syst}$J=20.7 Hz, 1H, $CH_{2b}$O-propargyl) 3.58-3.6 (m, 2H, —$CH_2$OH), 3.65 (s, 2H, DMTrO—$CH_2$—), 3.82 (s, 6H, $OCH_3$), 4.18 (dd, J=0.9 and 1.4 Hz, 2H, $CH_2$-CCH), 6.85-7.54 (m, 13H, arom.).

$^{13}$C NMR ($CDCl_3$, 100 MHz): 17.8, 40.8, 55.2, 58.7, 66.5, 68.9, 74.3, 74.5, 79.7, 86.0, 113.2, 126.7, 127.8, 128.1, 129.1, 130.1, 136.0, 145.0, 158.4.
HRFABMS (positive mode, nitrobenzylic alcohol) m/z: calcd for $C_{29}H_{32}O_5$ [M+H]$^+$ 460.2250. found 460.2248.

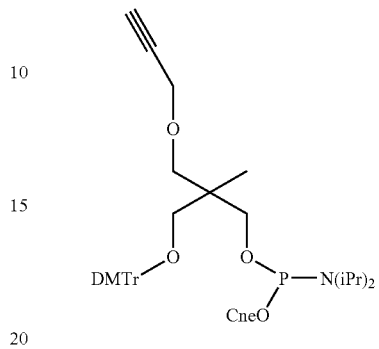

1-O-(4,4'-dimethoxytrityloxymethyl)-2-propargyloxymethyl-2-methyl-3-{O-[(2-cyanoethyl)-N,N-diisopropyl-phosphoramidite]-1,3-propanediol (18)

Same protocol than for 9 was applied starting from 325 mg 0.7 mmol of 17 gave 422 mg 92%.
$^1$H NMR ($CDCl_3$, 200 MHz): δ 1.00-1.21 (m, 15H, CH3), 2.42 (bs, 1H, CCH), 2.53-259 (t, 2H, J=6.5 Hz, —CH2CN), 3.03 (s, 2H, OCH2DMTr), 3.43-3.79 (m, 8H, OCH2-, CH, CH2OP, CH2Opropargyl), 3.82 (s, 6H, OCH3), 4.11-4.18 (bs, 2H, OCH2CC), 6.83-7.49 (m, 13H).
$^{13}$C NMR ($CDCl_3$, 100 MHz): δ 17.8, 20.3, 24.5, 24.6, 41.2, 41.3, 43.2, 43.3, 53.3, 55.2, 58.3, 58.5, 58.6, 58.7, 65.2, 66.5, 66.6, 66.7, 72.8, 72.9, 73.9, 80.2, 85.7, 113.0, 117.4, 126.5, 127.6, 128.4, 130.2, 136.5, 145.3, 158.5.
$^{31}$P NMR ($CDCN_3$, 80 MHz): δ 148.6, 148.7.
HRFABMS (positive mode, nitrobenzylic alcohol) m/z: calcd for $C_{38}H_{50}N_2O_6P_1$ [M+H]$^+$ 661.3383. found 661.3383.

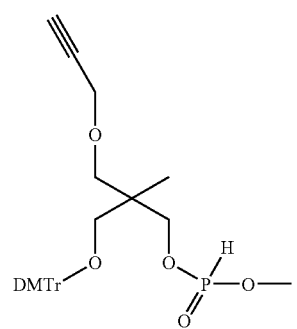

1-O-(4,4'-dimethoxytrityloxymethyl)-2-propargyloxymethyl-2-methyl-3-O—(H-phosphonate monoester triethylammonium)-1,3-propanediol (19)

Same protocol than for 10 starting from 17
Rf: 0.30 $CH_2Cl_2$, MeOH, $Et_3N$, (92.5:5:2.5, v/v/v),
$^1$H NMR (CD3CN, 300 MHz): $^1$H NMR ($CDCl_3$, 200 MHz): δ 1.00 (s, 3H, CH3), 2.75 (s, 1H, CCH), 3.03 (s, 2H, OCH2DMTr), 3.43-3.79 (m, 8H, OCH2-, CH2OP, CH2Opropargyl), 3.79 (s, 6H, OCH3), 4.11 (bs, 2H, OCH2CC), 6.58 (d, J HP=595 Hz, 1H, HP), 6.87-7.47 (m, 13H).

$^{31}$P NMR (CDCN$_3$, 80 MHz): δ 2.4.

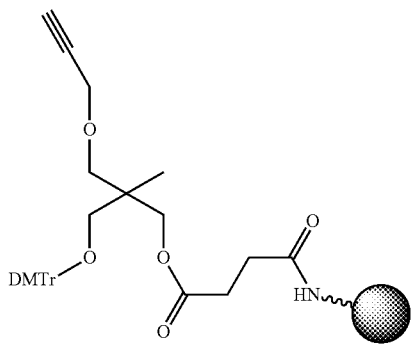

1-O-(4,4'-dimethoxytrityloxymethyl)-2-propargyloxymethyl-2-methyl-3-O-(succinic-LCAA CPG)-1, 3-propanediol (20)

Same protocol than for 11. Loading 32.2 μmol/g for LCAA CPG 500 Å and 30.1 μmol/g for LCAA CPG 1000 Å

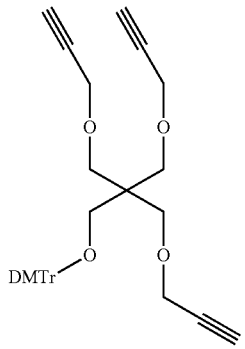

O-(4,4'-dimethoxytrityl)-tris-O-propargyl pentaerythritol. (12)

Sodium hydride (200 m g, 5.0 mmol, 60% in oil) was added to 1-O-(4,4'-dimethoxytrityl)-2,2-bis-propargyloxymethyl-1,3-propanediol (8) (514 mg, 1.0 mmol) dissolved in dry THF (8 mL) and cold at 0° C. The reaction was stirred for 10 min before adding propargyl bromide (0.57 mL, 5.0 mmol, 80% in toluene). The resulting milky solution was heated at 55° C. for 40 h. The solution was diluted with CH$_2$Cl$_2$ (8 mL) and the organic layer was washed with cold water (30 mL), brine (30 mL), dried (Na$_2$SO$_4$), filtered and evaporated. The residue was purified by chromatography on silica gel (Cyclohexane/CH$_2$Cl$_2$/Et$_3$N 80:18:2 to 75:22:2, v/v/v) affording the tris-propargylated pentaerythritol 12 (480 mg, 86%). R$_f$=0.451 (cyclohexane/CH$_2$Cl$_2$/Et$_3$N, 6:4:1, v/v/v). $^1$H NMR (CDCl$_3$, 200 MHz): δ 2.50 (t, J2.4 Hz, 3H, HC), 3.12 (s, 2H, CH2-ODMTr), 3.57 (s, 6H, —CH2Opropargyl), 3.82 (s, 6H, CH3O—), 4.09 (s, 6H, O—CH2-CCH), 6.82-7.50 (m, 13H, arom).

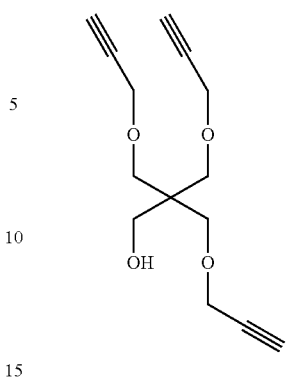

CAS 779349-07-4
Calvo-Flores, F. G. et al., *Organic Letters* 2, (2000) 2499-2502.

O-tris-propargyl-pentaerythritol. (13)

To a solution of O-(4,4'-dimethoxytrityl)-tris-O-propargyl pentaerythritol (12) (480 mg, 0.87 mmol) in CH$_2$Cl$_2$/MeOH (7:3, v/v) was added 4 mL of 10% para-toluenesulfonic acid in CH$_2$Cl$_2$/MeOH (7:3, v/v) and the solution was stirred for 30 min. Then 1.6 g of polyvinylpiridine was added and the heterogeneous colourless mixture was stirred for 15 min. The resin was filtered off and washed with 15 mL of CH$_2$Cl$_2$/MeOH (7:3, v/v). After evaporation the oil was purified by silica gel chromatography using cyclohexane with an increasing amount of ethyl acetate (0-50%), 100 mg 47%.

$^1$H NMR (CDCl$_3$, 200 MHz): δ 2.50 (t, J2.4 Hz, 3H, HC), 3.59 (s, 6H, —CH2Opropargyl), 3.72 (s, 2H, CH2OH), 4.16 (d, J2.4 Hz, 6H, O—CH2-CCH).

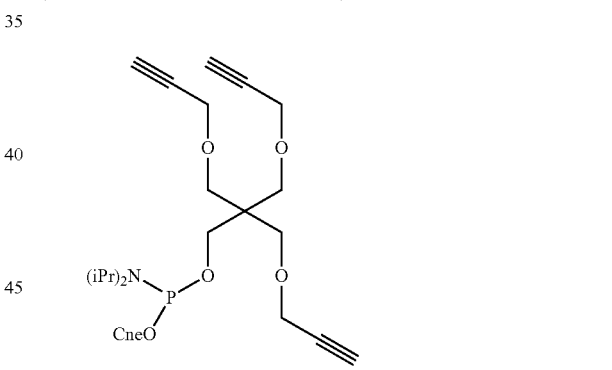

O-tris-propargyl-O-[(2-cyanoethyl)-N,N-diisopropyl-phosphoramidite]-pentaerythritol. (14)

Same protocol than for 9 was applied starting from 100 mg 0.4 mmol of 13.

120 mg, 79%. Rf: 0.65 (Cyclohexane/CH$_2$Cl$_2$/Et$_3$N, 74:25:1, v/v/v). $^1$H NMR (CDCl$_3$, 400 MHz): δ 1.18-1.20 (dd, J=1.9 Hz and 6.8 Hz 12H, CH3-) 2.41 (t, J=2.4 Hz, 3H, HC), 2.65 (td, J=1.9 Hz and 6.5 Hz, 2H, —CH2CN), 3.53 (s, 6H, —CH$_2$Opropargyl), 3.55-3.67 (m, 4H, O—CH2CH$_2$, CH, 3.81-3.89 (m, CH$_2$OP), 3.72 (s, 2H, CH2OH), 4.13 (d, J=2.4 Hz, 6H, O—CH2-CCH). $^{13}$C NMR (CDCl$_3$, 400 MHz): δ 20.4, 24.6, 24.7, 43.2, 45.2, 58.3, 58.4, 58.7, 62.3, 68.6, 74.2, 80.0, 117.7. $^{31}$P NMR (CDCN$_3$, 80 MHz): δ 150.0. HRFABMS (positive mode, nitrobenzylic alcohol) m/z: calcd for C$_{20}$H$_{31}$O$_4$N$_1$P$_1$ [M+H]$^+$ 380.1991. found 380.1975.

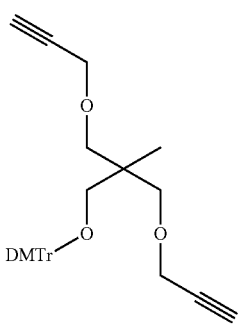

1,3-O-bis-propargyl-2-[O-(4,4'-dimethoxytrityloxymethyl)oxymethyl]-2-methyl-1,3-propanediol (21)

Same protocol than for 12 starting from 16.

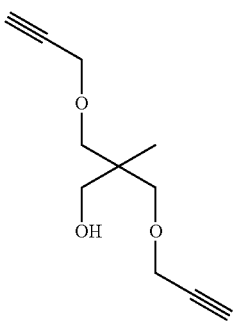

1,3-O-bis-propargyl-2-hydroxymethyl-2-methyl-1,3-propanediol (22)

Same protocol than for 13 starting from 21.

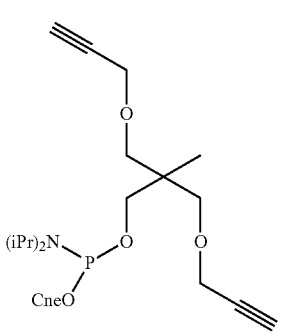

1,3-O-bis-propargyl-2-[(2-cyanoethyl)-N,N-diisopropyl-phosphoramidite]oxymethyl]-2-methyl-1,3-propanediol (23)

Same protocol than for 14 starting from 22.

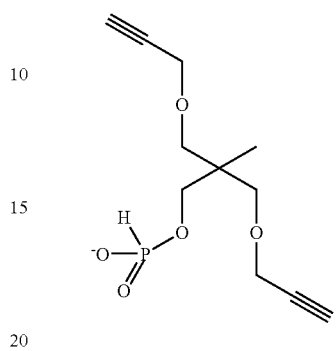

1,3-O-bis-propargyl-2-(H-phosphonate monoester triethylammonium)]oxymethyl]-2-methyl-1,3-propanediol (24)

Same protocol than for 19 starting from 22.

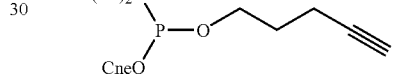

O-[(2-cyanoethyl)-N,N-diisopropyl-phosphoramidite] 4-propyn-1-ol (25)

4-propyn-1-ol (151 mg, 1.8 mmol) and 2-cyanoethyl tetraisopropylphosphorodiamidite (0.57 mL, 1.8 mmol) was coevaporated twice in dry acetonitrile. The residue was dissolved in dry $CH_2Cl_2$ (3 mL) and diisopropylammonium tetrazolide (154 mg, 0.9 mmol) was added. After 5 h of stirring at RT the solution was diluted with $CH_2Cl_2$ (50 mL) and the solution was washed with brine (2×100 mL). The organic layer was dried over Na2SO4 and evaporated to provide a pale yellow oil. The compound was purified by flash chromatography on silica gel using an increasing amount of $CH_2Cl_2$ in cyclohexane containing 5% of $Et_3N$.

350 mg, 68%.

Rf: 0.48 (Cyclohexane/$CH_2Cl_2$/$Et_3N$, 5:4:1, v/v/v). $^1$H NMR ($CDCl_3$, 200 MHz): δ 1.20 (d, J=7.2 Hz 12H, CH3-), 1.84 (quint, J=6.6 HZ, 2H, —CH2-CH2CCH), 1.96, (t, J=2.7 HZ, 1H, CCH), 2.32 (td, J=2.7 and 7.1 Hz, 2H, CH2-CCH) 2.65 (t, J=6.5 Hz, 2H, $CH_2CN$), 3.55-3.88 (m, 6H, PO—$CH_2$ and $CHMe_2$). $^{13}$C NMR ($CDCl_3$, 400 MHz): δ 15.1, 20.4, 24.6, 30.1, 43.0, 58.3, 61.9, 68.5, 83.7, 117.6. $^{31}$P NMR ($CDCN_3$, 80 MHz): δ 148.8.

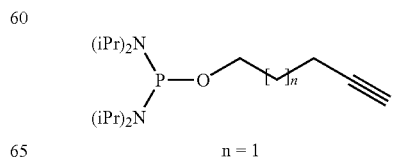

n = 1

4-propyn-1-ol tetraisopropylphosphorodiamidite (27)

To a solution of 4-propyn-1-ol (95 µL, 1.0 mmol) and Et₃N (278 mL, 2 mmol) in dry diethylether (2.5 mL), bis(diisopropylamino)chlorophosphine (267 mg, 1 mmol) was added and stirred for 2 h at RT. The solution was diluted with diethylether:triethylamine (9:1, v/v, 10 mL) and the salts were removed by filtration and washed. The solution was evaporated to the half and cyclohexane was added. Diethylether was removed by evaporation keeping cyclohexane. The solution was applied on a silica gel column (25 g) and the compound was purified using cyclohexane containing 6% of Et₃N.

280 mg, 89%.

Rf: 0.60 (Cyclohexane/CH₂Cl₂/Et₃N, 6:3:1, v/v/v). $^1$H NMR (CDCl₃, 200 MHz): δ 1.20 (dd, J=10.4 and 13.0 Hz 24H, CH3-), 1.83 (quint, J=6.6 HZ, 2H, —CH2-CH2CCH), 1.95, (t, J=2.6 HZ, 1H, CCH), 2.32 (td, J=2.6 and 7.1 Hz, 2H, CH2-CCH), 3.44-3.77 (m, 6H, PO—CH₂ and CHMe₂). $^{13}$C NMR (CD3CN, 400 MHz): δ 14.9, 23.4, 24.1, 30.5, 44.2, 62.4, 68.7, 83.9, 117.1. $^{31}$P NMR (CDCN₃, 80 MHz): δ 125.0.

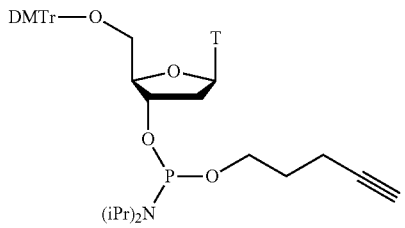

5'-O-Dimethoxytrityl-3'-O-[(4-propynyl)-N,N-diisopropyl-phosphoramidite] Thymidine (28)

Dry 5'-O-Dimethoxytrityl-thymidine (544.5, µmol) and dry diisopropylammonium tetrazolide (86 mg, 0.5 mmol) were dissolved in dry CH₂Cl₂ (8 mL), and 4-propyn-1-ol tetraisopropylphosphorodiamidite (377 mg, 1.2 mmol) was added. After 3 h of stirring the solution was diluted with ethyl acetate (80 mL) and the solution was washed with brine (2×150 mL). The organic layer was dried over Na₂SO₄ and evaporated. The compound was purified by flash chromatography on silica gel using an increasing amount of CH₂Cl₂ (14 to 44%) in cyclohexane containing 6% of Et₃N.

650 mg, 85%

Rf: 0.50 (Cyclohexane/CH₂Cl₂/Et₃N, 5:4:1, v/v/v).

$^1$H NMR (CDCl₃, 200 MHz): δ 1.07 (d, J=6.7, 3H, CH3-), 1.18 (d, J=6.8 Hz, 9H, CH3), 1.43 (bs, 3H, CH3T), 1.70-2.03 (m, 3H, CCH, —CH2-CH2CCH), 2.20-2.36 (m, 4H, H2', H2", CH2-CCH), 3.50-3.71 (m, 6H, H5', H5", O—CH2), 3.81 (s, 3H, OCH3), 4.17-4.22 (m, 1H, H4') 4.65-4.68 (m, 1H, H3'), 6.43-645 (m, 1H, H1'), 6.83-7.45 (m, 13H, arom), 7.68 (d, 1H, H6), 8.50 (bs, 1H, NH). $^{13}$C NMR (CD3CN, 400 MHz): δ 11.7, 15.1, 23.0, 24.5, 26.9, 30.0, 40.3, 43.1, 55.3, 61.9, 63.2, 68.7, 83.7, 84.8, 85.5, 85.9, 86.9, 111.2, 113.3, 127.2, 128.0, 128.2, 130.2, 135.3, 135.5, 135.7, 144.3, 150.4, 158.7, 163.9. $^{31}$P NMR (CDCN₃, 80 MHz): δ 148.3 and 148.7.

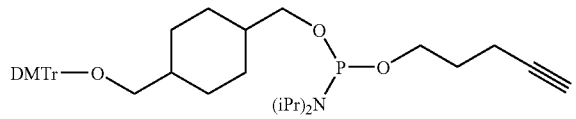

1-O-[(4-propynyl)-N,N-diisopropyl-phosphoramidite]-4-O-(Dimethoxytrityloxymethyl)cyclohexyl] methanol (29)

Same protocol than for 28 starting from 4-(Dimethoxytrityloxymethyl)cyclohexyl]methanol (332 mg, 0.74 mmol) afforded 450 mg 92%.

Rf: 0.17 (Cyclohexane/CH₂Cl₂/Et₃N, 7:2:1, v/v/v)

$^1$H NMR (CDCl₃, 200 MHz): δ 1.17-1.22 (d, 12H, CH3), 1.46-1.83 (m, 13H, CCH, cyclohexane, OCH2CH2CH2-), 2.29-2.34 (m, 2H, CH2CC), 2.89-2.92 (m, 2H, CH2-DMTr), 3.32-3.77 (m, 6H, CHMe2, CH2-cyclohexane, OCH2CH2-), 3.82 (s, 6H, CH3O), 6.83-7.50 (m, 13H, arom), $^{13}$C NMR (CD3CN, 400 MHz), 14.5, 24.0, 25.4, 25.9, 26.7, 29.1, 29.5, 30.1, 36.0, 36.7, 38.6, 39.5, 42.6, 42.7, 54.9, 61.4, 61.6, 66.0, 68.6, 68.9, 83.9, 85.4, 112.9, 117.3, 126.6, 127.7, 128.1, 130.0, 136.6, 145.7, 158.5, $^{31}$P NMR (CDCN₃, 80 MHz): δ 147.1

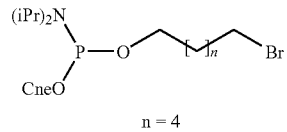

n = 4

O-[(2-cyanoethyl)-N,N-diisopropyl-phosphoramidite] 6-bromo-hexan-1-ol (31)

Same protocol than for 25 starting from 6-bromo-hexanol 325 mg 1.8 mmol gave 400 mg 60%.

$^1$H NMR (CDCl₃, 200 MHz): δ 1.17-1.21 (d, 12H, CH3), 1.44-1.88 (m, 8H, CH2), 2.62-2.69 (m, 2H, CH2CN), 3.39-3.87 (m, 8H, CH2O, CH2Br, CHMe2), $^{31}$P NMR (CDCN₃, 80 MHz): δ 148.5 ppm

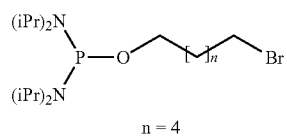

n = 4

6-bromo-hexan-1-ol tetraisopropylphosphorodiamidite (32)

Same protocol than for 27 starting from 6-bromo-hexanol 271.6 mg 1.5 mmol gave 410 mg 90%.

$^1$H NMR (CDCl₃, 200 MHz): δ 1.16-1.20 (dd, 24H, CH3), 1.42-1.47 (m, 4H, CH2), 1.56-1.65 (m, 2H, CH2CH2Br), 1.85-1.92 (m, 2H, OCH2CH2), 3.39-3.62 (m, 8H, CH₂O, CH2Br, CHMe2), $^{31}$P NMR (CDCN₃, 80 MHz): δ 125.3 ppm

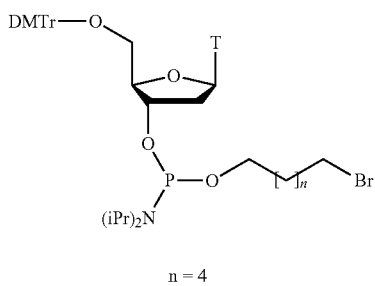

5'-O-(4,4'-dimethoxytrityl) 3'-O-[(6-bromohexyl) N,N-diisopropylamino phosphoramidite] thymidine 33

Same protocol than for 28 starting from 5'-(Dimethoxytrityloxymethyl)thymidine (300 mg, 0.54 mmol) and using 6-bromo-hexan-1-ol tetraisopropylphosphorodiamidite (32) afforded 377 mg 82%.

$^1$H NMR (CDCl$_3$, 200 MHz): δ 1.4-1.20 (m, 12H, CH3), 1.36-1.88 (m, 9H, CH3T, —CH2-), 2.50-2.65 (m, 2H, H2'H2"), 3.35-3.7 (m, 8H, H5'H5", CHMe2, CH2), 3.81 (s, 6H, CH3O—), 4.17-4.22 (m, 1H, H4'), 4.61-4.69 (m, 1H, H3'), 6.40-6.46 (m, 1H, H1'), 6.83-7.67 (m, 14H, H6, arom), $^{31}$P NMR (CDCN$_3$, 80 MHz): δ 147.8 and 148.3

Pentaerythrityl Nucleic Acids (PeNAs)

Figure 23:
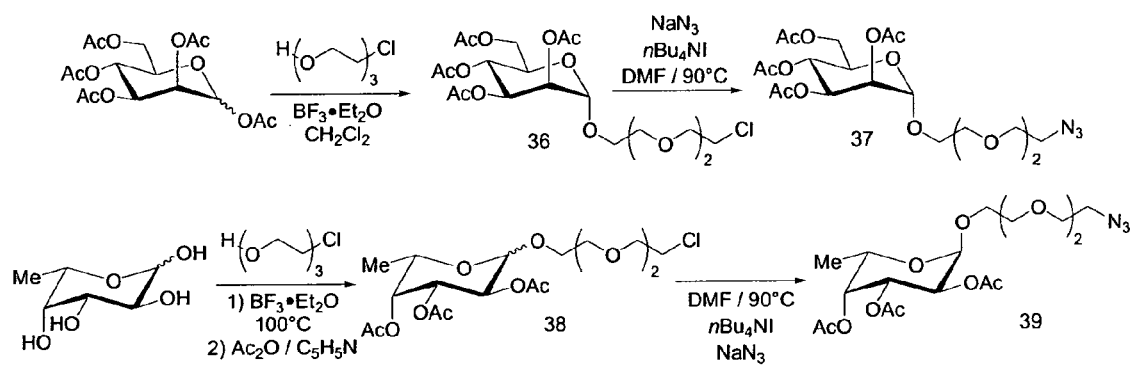
Figure 24:
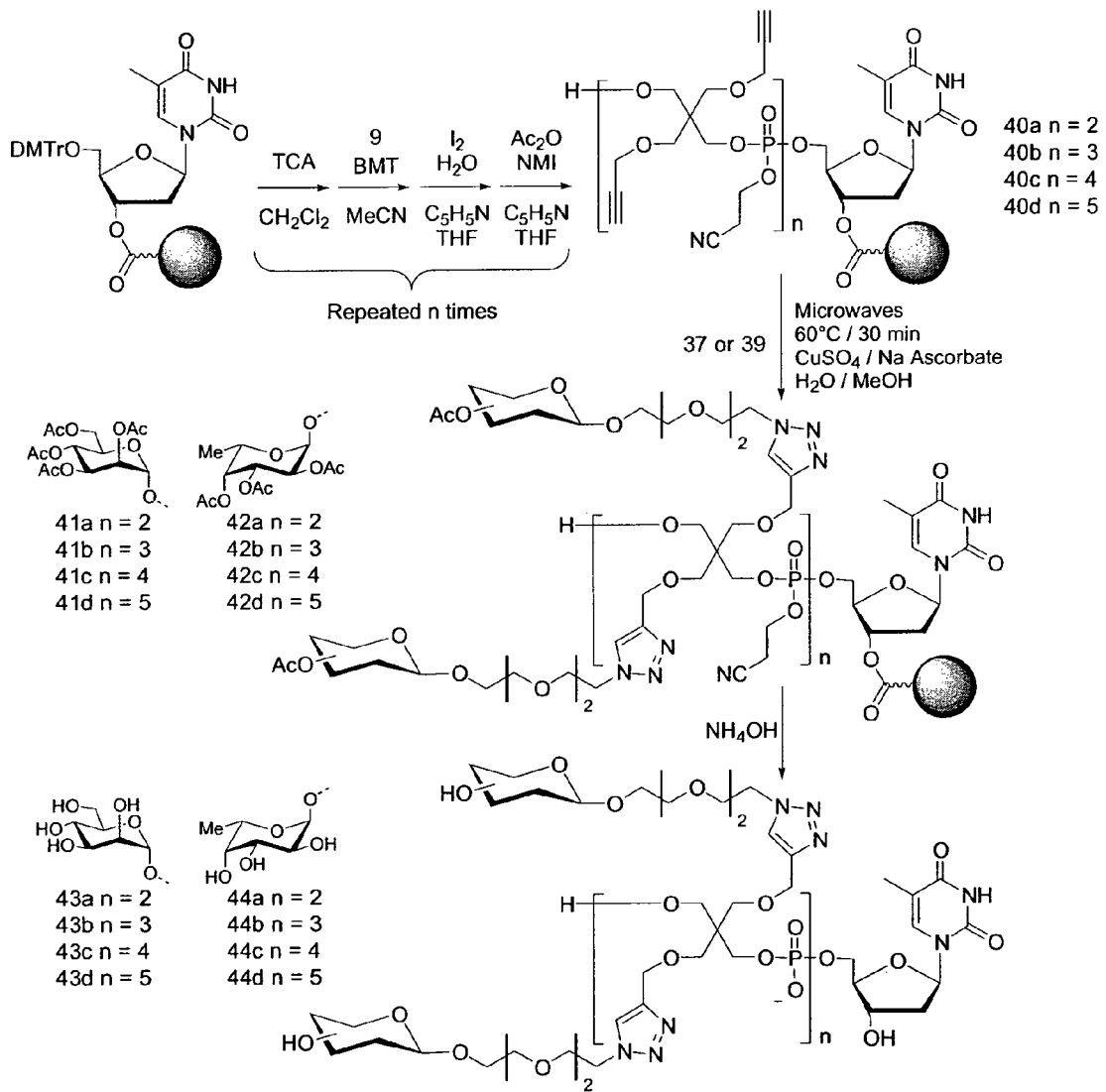

PeNAs based on a bis-2,2-saccharidyl-1,3-propanediol phosphodiester scaffold were prepared following the scheme hereunder:

The synthesis was based on a combination of oligonucleotide phosphoramidite chemistry on solid support and microwave assisted click chemistry. The PeNAs were incorporating only one nucleotide at the pseudo-3'-end as a tag for the determination of glycosylated PeNAs concentration by UV analysis. The propargylated PeNAs were conveniently prepared using a phosphoramidite dialkyne building block which was coupled several times using a DNA-like synthesis on solid support (FIG. 24). Carbohydrate moieties (FIG. 23) were then introduced from their azide derivatives by 1,3-dipolar cycloaddition ((a) Kolb, H. C. et al., Angew. Chem. Int. Ed. 2001, 40, 2004-2021; (b) Calvo-Flores, F. G. et al., F. Org. Lett. 2000, 2, 2499-2502. (c) Pérez-Balderas, F. et al., Org. Lett. 2003, 5, 1951-1954. (d) Chen, Q. et al., Carbohydr. Res. 2005, 340, 2476-2482. (e) Chittaboina, S. et al., Tetrahedron Lett. 2005, 46, 2331-2336. (f) Giguere, D. et al., Chem. Commun. 2006, 2379-2381. (g) Fernandez-Megia, E. et al., R. Macromolecules 2006, 39, 2113-2120. (h) Tejlera, J. et al., Carbohydr. Res. 2006, 341, 1353-1362) according to our previously reported procedure ((a) Bouillon, C. et al., J. Org. Chem. 2006, 71, 4700-4702. (b) Meyer, A. et al., Tetrahedron Lett. 2006 47, 8867-8871) leading to the desired PeNAs glycoclusters. The solid supported oligonucleotidic automated synthesis allows for a rapid and efficient preparation of propargylated PeNAs with control of the number of propargyl residues. Excess of reagents can be used to reach quantitative yields for each cycle with washings to remove them. Click chemistry on solid support is an efficient method for the rapid and efficient multiple labeling with azido carbohydrate derivatives. Finally, the cleavage from the solid support is achieved with concomitant deprotection of the glycosylated PeNAs and was used without further purification. The thymidine residue introduced at the pseudo-3'-end allows for the determination of the quantity of material present in the final solution.

Mannosylated and fucosylated PeNAs bearing 4, 6, 8 and 10 carbohydrate residues were synthesized as potential ligands for concanavalin A (ConA) and Pseudomonas aeruginosa lectin (PA-IIL). These two lectins are mannose and fucose binding lectins respectively. ConA is a legume lectin from Canavalia ensiformis consisting of a tetramer with four mannose/glucose binding sites and is now considered as a model system for studying protein-carbohdyrate interactions. Recently, a series of bacterial lectins have been identified that display micromolar affinities for their ligands. Among them, PA-IIL has been identified in Pseudomonas aeruginosa, an opportunistic bacterium that is life threatening for immunosuppressed and cystic fibrosis patients and that displays increasing resistance to antibiotics. PA-IIL is a fucose-binding lectin that has been well characterized for its high affinity for fucose and its interaction with other monosaccharides and oligosaccharides. The lectin is a tetramer and the high avidity provided by multivalent ligands could make these compounds of interest for anti-adhesive therapy against bacterial infection.

Experimental

Preparation of the Building Blocks

Automated synthesis requires orthogonally protected multifunctional scaffolds where each functional group can be activated selectively for reacting with the next entity. Pentaerythritol was selected as a tetrafunctional molecule which can be easily desymmetrized through simple reaction schemes. Mono-protection of pentaerythritol with dimethoxytrityl chloride provided the triol 7 (FIG. 14). Alkylation of 7 using a large excess of propargyl bromide yielded the bis-propargylated alcohol 8 in good yield. Reaction of alcohol 8 with 2-cyanoethyl tetraisopropylphosphorodiamidite activated with diisopropylammonium tetrazolide provided the expected phosphoramidite 9. This molecule is presenting a masked alcohol and a phosphoramidite moiety for the DNA-like chain elongation, as well as two propargyl residues for a further conjugation with carbohydrate azide derivatives using a [3+2]-cycloaddition reaction (a) Bouillon, C.; Meyer, A.; Vidal, S.; Jochum, A.; Chevolot, Y.; Cloarec, J.-P.; Praly, J.-P.; Vasseur, J.-J.; Morvan, F. J. Org. Chem. 2006, 71, 4700-4702. (b) Meyer, A., Bouillon, C., Vidal, S., Vasseur, J. J., and Morvan, F. Tetrahedron Lett. 2006 47, 8867-8871).

The synthesis of azido-carbohydrates is required for their conjugation by click chemistry on the propargyl residues. The control of the anomeric configuration of sugars is often crucial for optimal and selective binding to lectins. The O-acyl or Fischer stereoselective glycosylation methods were selected for the preparation of the α-D-mannoside or α-L-fucoside derivatives respectively (FIG. 23).

Glycosylation of mannose peracetate with chlorotriethylenglycol under Lewis acid activation afforded the chlorinated 1,2-trans mannoside 36. Subsequent azidation of the chloroglycol moiety provided the corresponding α-D-mannoside derivative 37. Glycosylation of L-fucose under Fischer conditions afforded a mixture of anomers (α/β 3/1) which was directly peracetylated to obtain L-fucoside 38. The separation of each anomer was unsuccessful at that point. Subsequent azidation of 6 afforded the corresponding azide derivative 39 with the same α/β distribution, each anomer was isolated pure after a flash silica gel column chromatography.

Solid-Supported Synthesis of PeNAs

The dialkyne phosphoramidite building block 9 was coupled starting from a commercial solid-supported thymidine applying a phosphoramidite elongation cycle on a DNA synthesizer. The thymidine present at the pseudo-3'-end of the polyglycosyl nucleic acid was used as a UV tag for HPLC analyses, as well as for the determination of concentrations in material in solution. The thymidine functionalized beads were subjected to a standard sequence of detritylation, phosphoramidite coupling under benzylthiotetrazole activation, oxidation and capping (FIG. 24) used for the synthesis of oligonucleotides. This cycle was repeated 2, 3, 4 and 5 times to obtain the oligoalkyne nucleic acid 40a-d respectively. After elongation, 1,3-dipolar cycloaddition was achieved on solid support using either the α-D-mannoside azide derivative 37 or the α-L-fucoside azide derivative 39 to obtain the fully protected glycosylated PeNAs 41a-d or 42a-d respectively. Aminolysis of the protecting groups (i.e. acetates and cyanoethyls) and concomitant cleavage from the solid support using concentrated aqueous ammonia afforded the fully deprotected glycosylated PeNAs 43α-d and 44a-d in solution with high purity and good yield. Each glycocluster was analyzed by HPLC and characterized by MALDI-ToF mass spectrometry (see supporting information). The quantities of available materials in solution were determined by UV measurements at 260 nm based on the extinction coefficient of thymidine.

1-Chloro-3,6-dioxaoct-8-yl 2,3,4,6-tetra-O-acetyl-α-D-mannopyranoside (36). A solution of 2-[2-(2-chloroethoxy)ethoxy]ethanol (3.66 mL, 25.2 mmol) and peracetylated D-mannose (6.56 g, 16.8 mmol) in anhydrous $CH_2Cl_2$ (50 mL) was cooled at 0° C. before dropwise addition of $BF_3.Et_2O$ (10.6 mL, 84 mmol). The reaction mixture was stirred at rt for 24 h then poured into saturated aqueous $NaHCO_3$ (300 mL). The aqueous layer was extracted with $CH_2Cl_2$ (2×200 mL). The organic layers were combined, dried ($Na_2SO_4$), filtered and evaporated. The oily residue was purified by flash silica gel column chromatography (PE then PE/EtOAc 3:2) to afford 36 (3.14 g, 37%) as a pale yellow oil. $^1H$ NMR ($CDCl_3$, 300 MHz): δ 1.96, 2.01, 2.08, 2.13 (4s, 4×3H, 4×$CH_3CO$), 3.58-3.82 (m, 12H, $OCH_2CH_2OCH_2CH_2OCH_2CH_2Cl$), 4.00-4.13 (m, 2H, H-5, H-6), 4.25 (dd, 1H, $J_{6',5}$=5.1 Hz, $J_{6',6}$=12.3 Hz, H-6'), 4.85 (d, 1H, $J_{1,2}$=1.6 Hz, H-1), 5.22-5.36 (m, 3H, H-2, H-3, H-4). $^{13}C$ NMR ($CDCl_3$, 75 MHz): δ 20.6, 20.7, 20.8, 21.0 (4s, 4×$CH_3CO$), 42.7 ($CH_2Cl$), 62.3 (C-6), 66.0, 68.3, 69.0, 69.5 (4s, C-2 to C-5), 67.3, 70.0, 70.56, 70.63, 71.3 (5s, 5×$CH_2O$), 97.6 (C-1), 169.6, 169.8, 170.0, 170.6 (4s, 4×$CH_3CO$). $[α]_D$=+42 (c=1/$CH_2Cl_2$). ESIMS (positive mode) m/z: 521 [M+Na]$^+$. HRESIMS (positive mode) m/z: calcd for $C_{20}H_{31}Cl_1O_{12}Na_1$ [M+Na]$^+$ 521.1402. found 521.1403.

1-Azido-3,6-dioxaoct-8-yl 2,3,4,6-tetra-O-acetyl-α-D-mannopyranoside (37). A solution of 36 (2.9 g, 5.8 mmol), sodium azide (1.89 g, 29.1 mmol) and $nBu_4NI$ (4.3 g, 11.6 mmol) in anhydrous DMF (20 mL) was stirred at 90° C. for 24 h. The solution was cooled to rt then diluted with EtOAc (300 mL). The organic layer was washed with water (3×200 mL), dried ($Na_2SO_4$), filtered and evaporated. The oily residue was purified by flash silica gel column chromatography (PE then PE/EtOAc 1:1) to afford 37 (2.54 g, 86%) as a pale yellow oil. $^1H$ NMR ($CDCl_3$, 300 MHz): δ 1.96, 2.02, 2.08, 2.13 (4s, 4×3H, 4×$CH_3CO$), 3.37 (t, 2H, J=5.0 Hz, $CH_2N_3$), 3.60-3.72 (m, 9H, $OCH_2CH_2O$), 3.74-3.84 (m, 1H, $OCH_2$), 4.00-4.15 (m, 2H, H-5, H-6), 4.27 (dd, 1H, $J_{6',5}$=5.1 Hz, $J_{6',6}$=12.4 Hz, H-6'), 4.85 (d, 1H, $J_{1,2}$=1.5 Hz, H-1), 5.20-5.37 (m, 3H, H-2, H-3, H-4). $^{13}C$ NMR ($CDCl_3$, 75 MHz): δ 20.62, 20.63, 20.7, 20.8 (4s, 4×$CH_3CO$), 50.6 ($CH_2N_3$), 62.3 (C-6), 66.0, 68.3, 69.0, 69.5 (4s, C-2 to C-5), 67.2, 69.97, 70.02, 70.6, 70.7 (5s, 5×$CH_2O$), 97.6 (C-1), 169.6, 169:8, 170.0, 170.6 (4s, 4×$CH_3CO$)-$[α]_D$=+34 (c=1/$CH_2Cl_2$). ESIMS (positive mode) m/z: 528 [M+Na]$^+$. HRESIMS (positive mode) m/z: calcd for $C_{20}H_{31}N_3O_{12}Na_1$ [M+Na]$^+$ 528.1805. found 528.1801.

1-Azido-3,6-dioxapent-8-yl 2,3,4-tri-O-acetyl-α-L-fucopyranoside (39). A solution of L-fucose (1 g, 6.1 mmol) and 2-[2-(2-chloroethoxy)ethoxy]ethanol (3 mL, 20.6 mmol) was stirred at rt for 5 min followed by the dropwise addition of $BF_3.Et_2O$ (1.54 mL, 12.2 mmol). The reaction mixture was stirred at 100° C. for 5 h and the solution turned yellow then dark brown. The crude mixture was then poured into pyridine (35 mL) and acetic anhydride (7 mL) was then added at 0° C. The solution was stirred at rt for 48 h then poured into iced water (100 mL) and the aqueous layer was extracted with EtOAc (150 mL). the organic layer was washed with water (100 mL), saturated aqueous $NaHCO_3$ (100 mL), dried ($Na_2SO_4$), filtered, evaporated to dryness and co-evaporated with toluene (4×30 mL). The oily residue was purified by flash silica gel column chromatography ($CH_2Cl_2$ then $CH_2Cl_2$/EtOAc 4:1) to afford the intermediate 1-chloro-3,6-dioxapent-8-yl 2,3,4-tri-O-acetyl-L-fucopyranoside 38 (718 mg) as a colourless oil and as a α/β (3:1) mixture of anomers. A solution of 38 (718 mg, 1.63 mmol), sodium azide (1.06 g, 16.3 mmol) and n-tetrabutylammonium iodide (300 mg, 0.81 mmol) in DMF (20 mL) was stirred at 90° C. for 16 h. The solution was diluted with water (100 mL) and the aqueous layer extracted with $CH_2Cl_2$ (2×150 mL). The organic layers were combined, dried ($Na_2SO_4$), filtered and evaporated to dryness. The oily residue was purified by flash silica gel column chromatography (Hexane/$CHCl_3$ then Hexane/$CHCl_3$/Acetone 2:1:1) to afford 39 (441 mg, 16%) as a pale yellow oil. A first crop of the α anomer (113 mg) was obtained followed by two additional crops of 226 mg and 102 mg of α/β mixture of anomers in 4:1 and 1:1 ratio respectively. $^1H$ NMR ($CDCl_3$, 300 MHz): δ 1.13 (d, 3H, $J_{6,5}$=6.6 Hz, H-6), 1.98, 2.07, 2.16 (3s, 3×3H, 3×$CH_3CO$), 3.40 (t, 2H, J=5.2 Hz, $CH_2N_3$), 3.60-3.85 (m, 11H, $OCH_2$, H-5), 4.23 (q, 1H, $J_{5,6}$=6.6 Hz, H-5), 5.10-5.17 (m, 2H), 5.30 (dd, 1H, $J_{2,1}$=1.1 Hz, $J_{2,3}$=3.4 Hz, H-2), 5.34-5.40 (m, 1H).

General procedure for the automated synthesis of propargylated PeNAs (40a-d). The syntheses of propargylated PeNAS 40a-d were performed on a DNA synthesizer (381A, ABI) on 1 μmolar scale using standard phosphoramidite chemistry with commercial LCAA-CPG solid-supported 5'-O-dimethoxytrityl-thymidine (500 Å) and phosphoramidite 9. The pseudo-oligonucleotidic chain elongation cycle was as follows: Dedimethoxytritylation was performed with trichloroacetic acid (3% in $CH_2Cl_2$) for 60 s; coupling was performed with 36 (0.09 M in acetonitrile, 18 molar eq) activated with benzylthiotetrazole (0.3 M in acetonitrile) for 60 s; oxidation was performed with $I_2$ (0.1 M in THF/pyridine/water 90:5:5, v/v/v) for 20 s and capping was performed successively with a 1:1 solution of Cap A ($Ac_2O$ in pyridine/THF 1:1:8, v/v/v) and Cap B (10% N-methyl-imidazole in THF) for 16 s.

General procedure for the synthesis of glycosylated PeNAs (43a-d and 44a-d). Solid-supported propargylated PeNAs 40a-d were transferred into a microwave vial and azido carbohydrate derivatives 37 or 39 (0.6 M in MeOH, 5 molar eq per alkyne), $CuSO_4$ (0.1 M in water, 0.2 molar eq per alkyne), sodium ascorbate (0.25 M in water, 1 molar eq per alkyne) were added and the solution was completed with water and MeOH to obtain a final volume of 200 μL water/MeOH (1/1). The vial was sealed then irradiated with microwaves for 30 min at 60° C. to afford 41a-d or 42a-d respectively. Treatment of the beads with concentrated aqueous ammonia for 2 h at rt afforded the oligoGNAs 43a-d or 44a-d respectively. The concentration of the glycosylated PeNAs was determined by UV measurement at 260 nm based on the extinction coefficient of thymidine ($ε^{260nm}$=8700 L·mol$^{-1}$·cm$^{-1}$) and characterized by MALDI-ToF mass spectrometry (Table 2).

TABLE 2

Quantities and MALDI-ToF data obtained for PeNAs 43a-d and 44a-d.

| Glycosylated PeNAs | Quantity obtained (mg) | Number of moles (μmol) | [M − H]⁻ Calcd. | [M − H]⁻ Found |
|---|---|---|---|---|
| 43a | 10.32 | 00.56 | 2138.99 | 2138.01 |
| 43b | 20.22 | 00.66 | 3087.99 | 3087.39 |
| 43c | 20.52 | 00.57 | 4036.74 | 4036.87 |
| 43d | 30.18 | 00.58 | 4985.62 | 4985.29 |
| 44a | 00.88 | 00.43 | 2074.99 | 2075.29 |
| 44b | 10.89 | 00.63 | 2991.87 | 2992.12 |
| 44c | 0.43 | 00.62 | 3908.75 | 3908.22 |
| 44d | 0.77 | 00.57 | 4825.63 | 4825.43 |

The invention claimed is:

1. Molecules of formula (XIII):

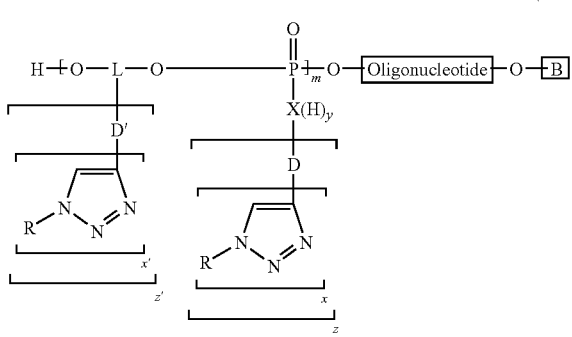

(XIII)

wherein

X is selected from N, O, S, an alcane di-yl comprising 1 to 12 carbon atoms; preferentially X is selected from N, O;

m is an integer, m≧1

L is a linker which may be selected from the following list: alcane poly-yl functions with 1 to 12 carbon atoms, linear branched or cyclic possibly interrupted by one or several oxygen (—O—), nitrogen (—NH—, —N═) or sulphur (—S—) bridges or phosphodiester [—O—(O⁻)P(═O)—O—] bridges;

x is an integer, 30≧x≧1;

x' is an integer, 30≧x'≧1;

D is a linker between X and the carbon in position 4 of the triazole ring;

D' is a linker between L and the carbon in position 4 of the triazole ring;

y is 0, 1 or 2;

z and z' are integers, z and z'≧0, at least one of z and z' is ≧1;

B is selected from H, a solid support or a tag;

the oligonucleotide is substituted either on its 3'-extremity, on its 5'-extremity or inside of the sequence;

R is a molecule of interest.

2. Molecules according to claim 1 of formula (III):

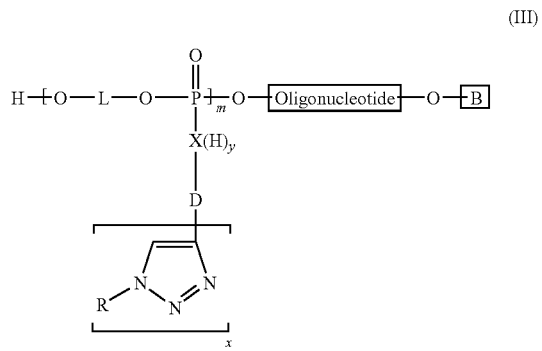

(III)

wherein

X is selected from N, O, S, an alcane di-yl comprising 1 to 12 carbon atoms; preferentially X is selected from N, O;

m is an integer, m≧1

L is a linker which may be selected from the following list: alcane di-yl functions with 1 to 12 carbon atoms, linear branched or cyclic possibly interrupted by one or several oxygen (—O—), nitrogen (—NH—, —N═) or sulphur (—S—) bridges or phosphodiester [—O—(O⁻)P(═O)—O—] bridges;

x is an integer, 30≧x≧1;

D is a linker between X and the carbon in position 4 of the triazole ring;

y is 0, 1 or 2;

B is selected from H, a solid support or a tag;

the oligonucleotide is substituted either on its 3'-extremity, on its 5'-extremity or inside of the sequence;

R is a molecule of interest.

3. Molecule according to claim 1, wherein R is selected from the group consisting of carbohydrates and their derivatives.

4. Molecule according to claim 3, wherein R is selected from the group consisting of mono and polysaccharides grafted on one of their extremities by a —CH₂—(CH₂—O—CH₂)ᵣ—CH₂— groups, with r an integer, r≧1.

5. Molecule according to claim 1, wherein R is selected from the group consisting of amino acids and peptides.

6. Molecule according to claim 1, wherein R is selected from the group consisting of fluorescent tags.

7. Molecule according to claim 1, wherein D is selected from alcane poly-yl groups comprising 1 to 36 carbon atoms, and alcane poly-yl groups comprising 1 to 36 carbon atoms interrupted by one or several oxygen bridges.

8. Molecule according to anyone of claim 7, wherein L is a linker selected from:

an alcane poly-yl with 1 to 12 carbon atoms, linear, branched or cyclic;

a group

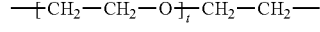

with t an integer selected from 1, 2, 3, 4, 5, 6;

an alcane poly-yl with 1 to 12 carbon atoms including an oxygen comprising heterocycle.

9. Molecule according to anyone of claim 1, wherein one or several phosphate function(s) of the oligonucleotide chain has been replaced by a phosphoramidate group of the type:

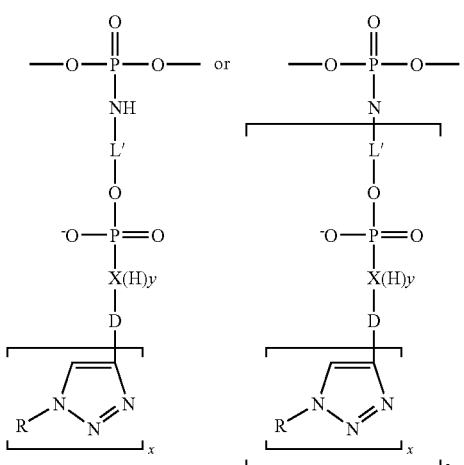

wherein L' is an alcane di-yl chain comprising 1 to 12 carbon atoms.

10. Method for the preparation of a molecule according to claim 1, wherein said method comprises the step of reacting an azido function attached to R with an alkyne substituted phosphodiester derivative of the oligonucleotide:

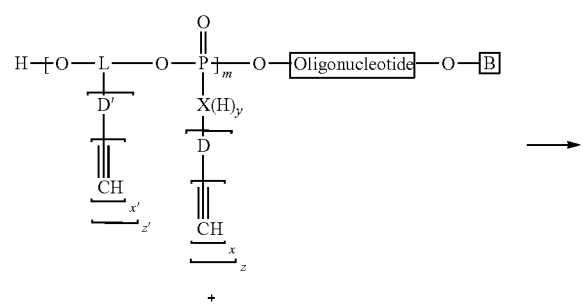

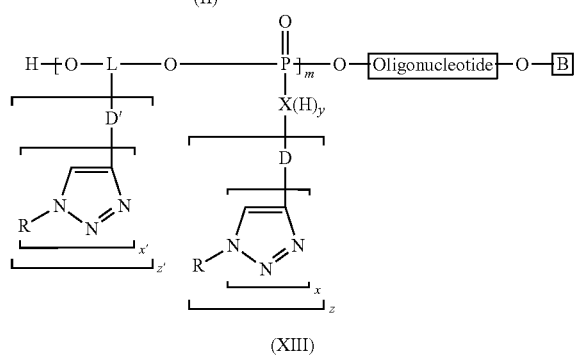

(XIII)

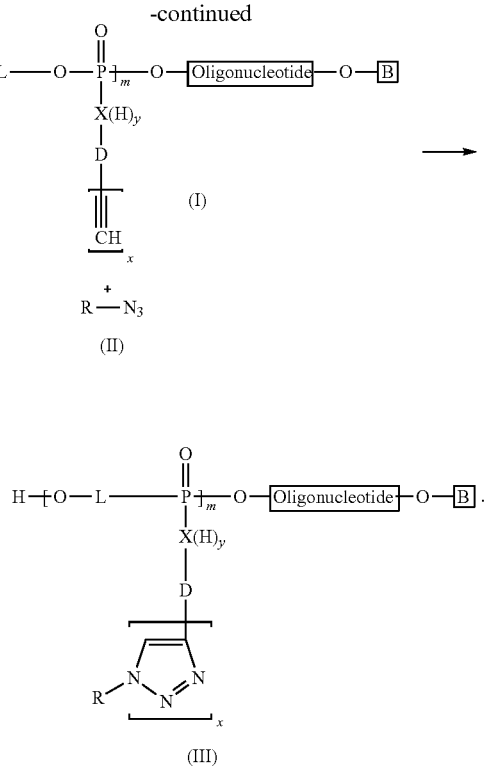

11. Method according to claim 10, wherein the molecule (I) or (XIV) is in solution.

12. Method according to claim 10, wherein the molecule (I) or (XIV) comprises a grafting onto a solid support.

13. Method according to claim 10, wherein the reaction is made with application of microwaves.

14. Method according to claim 10, wherein the reaction is made with heating at a temperature in which the reactive medium is heated to a temperature comprised between 30 and 100° C.

15. Method according to claim 10, wherein the reaction is performed with the presence of a Copper (Cu$^+$) catalyst and sodium ascorbate.

16. Method according to claim 10, wherein the oligonucleotide of formula (I) or (XIV) is 3'-substituted, and wherein it further comprises another step of oligonucleotide synthesis, so that other nucleotide units are added to the chain, and another step according to claim 10 is performed.

17. A solid support grafted by a molecule as depicted in formula (XIII) according to claim 1.

* * * * *